United States Patent
Nakagami et al.

(10) Patent No.: US 10,233,215 B2
(45) Date of Patent: Mar. 19, 2019

(54) PEPTIDE AND USE THEREOF

(71) Applicant: OSAKA UNIVERSITY, Suita (JP)

(72) Inventors: Hironori Nakagami, Suita (JP); Ryuichi Morishita, Suita (JP); Hiroshi Koriyama, Suita (JP); Akiko Tenma, Suita (JP)

(73) Assignee: OSAKA UNIVERSITY, Suita (JP)

( * ) Notice: Subject to any disclaimer, the term of this patent is extended or adjusted under 35 U.S.C. 154(b) by 0 days.

(21) Appl. No.: 16/134,153

(22) Filed: Sep. 18, 2018

(65) Prior Publication Data

US 2019/0002505 A1   Jan. 3, 2019

Related U.S. Application Data

(62) Division of application No. 15/514,310, filed as application No. PCT/JP2015/077139 on Sep. 25, 2015, now Pat. No. 10,112,978.

(30) Foreign Application Priority Data

Sep. 26, 2014 (JP) ................................ 2014-197386

(51) Int. Cl.
| | | |
|---|---|---|
| *A61K 39/39* | (2006.01) | |
| *C07K 7/08* | (2006.01) | |
| *A61K 8/64* | (2006.01) | |
| *A61Q 7/00* | (2006.01) | |
| *A61K 38/00* | (2006.01) | |
| *A61K 39/00* | (2006.01) | |

(52) U.S. Cl.
CPC .................. *C07K 7/08* (2013.01); *A61K 8/64* (2013.01); *A61K 38/00* (2013.01); *A61K 39/39* (2013.01); *A61Q 7/00* (2013.01); *A61K 2039/55516* (2013.01)

(58) Field of Classification Search
CPC ............ A61K 8/64; A61K 2039/55516; A61K 2800/78; A61K 38/00; A61K 38/10; A61K 39/39; C07K 7/08; C07K 7/06; A23L 33/18
See application file for complete search history.

(56) References Cited

U.S. PATENT DOCUMENTS

| | | |
|---|---|---|
| 8,533,541 B2 | 9/2013 | Iwashita et al. |
| 9,872,825 B2 | 1/2018 | Nakagami et al. |
| 2007/0281888 A1 | 12/2007 | Nishikawa et al. |
| 2012/0005545 A1 | 1/2012 | Iwashita |
| 2012/0052104 A1 | 3/2012 | Gemba et al. |
| 2012/0122766 A1 | 5/2012 | Gemba et al. |
| 2012/0172287 A1 | 7/2012 | Gemba et al. |
| 2017/0275336 A1 | 9/2017 | Nakagami et al. |

FOREIGN PATENT DOCUMENTS

| | | |
|---|---|---|
| JP | 2008-247874 A | 10/2008 |
| JP | 2012-014583 A | 1/2012 |
| WO | WO 2005/090564 A1 | 9/2005 |
| WO | WO 2008/096814 A1 | 8/2008 |
| WO | WO 2008/096816 A1 | 8/2008 |
| WO | WO 2010/061915 A1 | 6/2010 |
| WO | WO 2010/101237 A1 | 9/2010 |
| WO | WO 2010/137594 A1 | 12/2010 |
| WO | WO 2014/157485 A1 | 10/2014 |

OTHER PUBLICATIONS

Nakagami et al., "Modification of a novel angiogenic peptide, AG30, for the development of novel therapeutic agents," *J. Cell. Mol. Med.*, 16(7): 1629-1639 (2012).

Nishikawa et al., "Development of a novel antimicrobial peptide, AG-30, with angiogenic properties," *J. Cell. Mol. Med.*, 12(3): 1-13 (2008).

Japanese Patent Office, International Search Report in International Patent Application No. PCT/JP2015/077139 (dated Dec. 1, 2015).

*Primary Examiner* — Padmavathi Baskar
(74) *Attorney, Agent, or Firm* — Leydig, Voit & Mayer, Ltd.

(57) ABSTRACT

The invention provides a peptide and an immunostimulant or hair grower containing the peptide as an active ingredient, as well as a method for hair growth or regrowth promotion by administering an effective amount of the peptide to a mammal. The peptide has 23 or less amino acids and includes the amino acid sequence LHRLKRLRKRL (SEQ ID NO: 1), preferably the amino acid sequence LHRLKRL-RKRLK (SEQ ID NO: 9).

8 Claims, 18 Drawing Sheets

Specification includes a Sequence Listing.

SEQUENCE LISTING

<160> NUMBER OF SEQ ID NOS: 14

<210> SEQ ID NO 1
<211> LENGTH: 11
<212> TYPE: PRT
<213> ORGANISM: Artificial Sequence
<220> FEATURE:
<223> OTHER INFORMATION: synthesized peptide

```
<400> SEQUENCE: 1

Leu His Arg Leu Lys Arg Leu Arg Lys Arg Leu
1               5                   10

<210> SEQ ID NO 2
<211> LENGTH: 20
<212> TYPE: PRT
<213> ORGANISM: Artificial Sequence
<220> FEATURE:
<223> OTHER INFORMATION: synthesized peptide

<400> SEQUENCE: 2

Glu Leu Lys Leu Ile Phe Leu His Arg Leu Arg Leu Arg Lys Arg
1               5                   10                  15

Leu Lys Arg Lys
            20

<210> SEQ ID NO 3
<211> LENGTH: 18
<212> TYPE: PRT
<213> ORGANISM: Artificial Sequence
<220> FEATURE:
<223> OTHER INFORMATION: synthesized peptide

<400> SEQUENCE: 3

Glu Leu Lys Leu Ile Phe Leu His Arg Leu Arg Leu Arg Lys Arg
1               5                   10                  15

Leu Lys

<210> SEQ ID NO 4
<211> LENGTH: 16
<212> TYPE: PRT
<213> ORGANISM: Artificial Sequence
<220> FEATURE:
<223> OTHER INFORMATION: synthesized peptide

<400> SEQUENCE: 4

Glu Leu Lys Leu Ile Phe Leu His Arg Leu Lys Arg Leu Arg Lys Arg
1               5                   10                  15

<210> SEQ ID NO 5
<211> LENGTH: 14
<212> TYPE: PRT
<213> ORGANISM: Artificial Sequence
<220> FEATURE:
<223> OTHER INFORMATION: synthesized peptide

<400> SEQUENCE: 5

Glu Leu Lys Leu Ile Phe Leu His Arg Leu Lys Arg Leu Arg
1               5                   10

<210> SEQ ID NO 6
<211> LENGTH: 18
<212> TYPE: PRT
<213> ORGANISM: Artificial Sequence
<220> FEATURE:
<223> OTHER INFORMATION: synthesized peptide

<400> SEQUENCE: 6

Leu Lys Leu Ile Phe Leu His Arg Leu Lys Arg Leu Arg Lys Arg Leu
1               5                   10                  15

Lys Arg

<210> SEQ ID NO 7
```

```
<211> LENGTH: 16
<212> TYPE: PRT
<213> ORGANISM: Artificial Sequence
<220> FEATURE:
<223> OTHER INFORMATION: synthesized peptide

<400> SEQUENCE: 7

Lys Leu Ile Phe Leu His Arg Leu Lys Arg Leu Arg Lys Arg Leu Lys
1               5                   10                  15

<210> SEQ ID NO 8
<211> LENGTH: 14
<212> TYPE: PRT
<213> ORGANISM: Artificial Sequence
<220> FEATURE:
<223> OTHER INFORMATION: synthesized peptide

<400> SEQUENCE: 8

Leu Ile Phe Leu His Arg Leu Lys Arg Leu Arg Lys Arg Leu
1               5                   10

<210> SEQ ID NO 9
<211> LENGTH: 12
<212> TYPE: PRT
<213> ORGANISM: Artificial Sequence
<220> FEATURE:
<223> OTHER INFORMATION: synthesized peptide

<400> SEQUENCE: 9

Leu His Arg Leu Lys Arg Leu Arg Lys Arg Leu Lys
1               5                   10

<210> SEQ ID NO 10
<211> LENGTH: 12
<212> TYPE: PRT
<213> ORGANISM: Artificial Sequence
<220> FEATURE:
<223> OTHER INFORMATION: synthesized peptide

<400> SEQUENCE: 10

Phe Leu His Arg Leu Lys Arg Leu Arg Lys Arg Leu
1               5                   10

<210> SEQ ID NO 11
<211> LENGTH: 13
<212> TYPE: PRT
<213> ORGANISM: Artificial Sequence
<220> FEATURE:
<223> OTHER INFORMATION: synthesized peptide

<400> SEQUENCE: 11

His Arg Leu Lys Arg Leu Arg Lys Arg Leu Lys Arg Lys
1               5                   10

<210> SEQ ID NO 12
<211> LENGTH: 20
<212> TYPE: PRT
<213> ORGANISM: Artificial Sequence
<220> FEATURE:
<223> OTHER INFORMATION: synthesized peptide

<400> SEQUENCE: 12

Met Leu Lys Leu Ile Phe Leu His Arg Leu Lys Arg Met Arg Lys Arg
1               5                   10                  15

Leu Lys Arg Lys
            20
```

```
<210> SEQ ID NO 13
<211> LENGTH: 19
<212> TYPE: PRT
<213> ORGANISM: Artificial Sequence
<220> FEATURE:
<223> OTHER INFORMATION: synthesized peptide

<400> SEQUENCE: 13

Leu Lys Leu Ile Phe Leu His Arg Leu Lys Arg Met Arg Lys Arg Leu
1               5                   10                  15

Lys Arg Lys

<210> SEQ ID NO 14
<211> LENGTH: 29
<212> TYPE: PRT
<213> ORGANISM: Artificial Sequence
<220> FEATURE:
<223> OTHER INFORMATION: synthesized peptide

<400> SEQUENCE: 14

Glu Leu Lys Leu Ile Phe Leu His Arg Leu Lys Arg Leu Arg Lys Arg
1               5                   10                  15

Leu Lys Arg Lys Leu Arg Leu Trp His Arg Lys Arg Tyr
            20                  25
```

PEPTIDE AND USE THEREOF

CROSS-REFERENCE TO RELATED APPLICATIONS

This patent application is a divisional of copending U.S. patent application Ser. No. 15/514,310, filed on Mar. 24, 2017, which is the U.S. national phase of International Patent Application No. PCT/JP2015/077139, filed Sep. 25, 2015, which claims the benefit of Japanese Patent Application No. 2014-197386, filed on Sep. 26, 2014, which are incorporated by reference in their entireties herein.

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 3,902 bytes ASCII (Text) file named "740543SequenceListing.txt," created Sep. 14, 2018.

TECHNICAL FIELD

The present invention relates to a novel peptide, and also relates to an immunostimulant, a vaccine adjuvant, a vaccine composition or a hair grower each of which contains the peptide.

BACKGROUND ART

Adjuvants are substances which are administered as a mixture with an antigen to a living body to enhance immune responses against the antigen. Adjuvants are classified into ones that induce Th1-type response, ones that induce Th2-type response and ones that induce both Th1-type response and Th2-type response. Generally, vaccine therapy involves the use of adjuvants, and such adjuvants must be capable of facilitating the recognition of antigens in hosts and the local retention thereof for a prolonged time. However, since adjuvants have the potential to trigger inflammation, they can cause pain, swelling and other side reactions at the site of administration, which are often problematic. Such side reactions at the site of administration have often been pointed to as problems in some of the vaccines clinically applied so far. Alum (aluminum hydroxide) has been long used as an adjuvant and is relatively highly safe. However, more effective adjuvants are desired for the improvement of vaccine efficacy.

There are many people who are concerned about alopecia caused by aging, genetic predisposition, social stress or other reasons. Under such a circumstance, various products, such as hair growers for promotion of hair regrowth and anti-alopecia agents for prevention of hair loss, have been developed.

A known example is an anti-alopecia agent in which a soybean protein-derived peptide having a specific sequence is contained as an active ingredient (Patent Literature 1).

The present inventors previously discovered a 30-amino-acid peptide having angiogenic and antimicrobial activities, which peptide was designated as AG30 (Non Patent Literature 1 and Patent Literature 2). Subsequently, the present inventors have modified this peptide for the improvement of its angiogenic and antimicrobial activities (Non Patent Literature 2, Patent Literature 3, Patent Literature 4, Patent Literature 5 and Patent Literature 6).

CITATION LIST

Patent Literature

Patent Literature 1: JP-A 2008-247874
Patent Literature 2: WO 2005/090564
Patent Literature 3: WO 2010/061915
Patent Literature 4: WO 2010/101237
Patent Literature 5: WO 2010/137594
Patent Literature 6: JP-A 2012-14583

Non Patent Literature

Non Patent Literature 1:
J. Cell. Mol. Med., 2008; 13: 535-46
Non Patent Literature 2:
J. Cell. Mol. Med. Vol. 16, No. 7, 2012, pp. 1629-1639

SUMMARY OF INVENTION

Technical Problem

An object of the present invention is to provide a novel short-chain peptide having immunostimulatory effect or hair growth and/or regrowth promoting effect, and a novel immunostimulant, vaccine adjuvant, vaccine composition or hair grower containing the peptide.

Solution to Problem

In order to achieve the above-mentioned object, the present inventors made further modifications to AG30, and as a result, found a peptide of 23 or less amino acid residues having immunostimulatory effect or hair growth and/or regrowth promoting effect. Based on this finding, the present inventors completed the present invention. The present invention includes the following.

[1] A peptide of 23 or less amino acids comprising the amino acid sequence LHRLKRLRKRL (SEQ ID NO: 1).
[2] The peptide according to the above [1], wherein the peptide comprises the amino acid sequence LHRLKRLRKRLK (SEQ ID NO: 9).
[3] The peptide according to the above [1] or [2], wherein the peptide comprises the amino acid sequence ELKLIFLHRLKRLRKRLKRK (SEQ ID NO: 2) or an amino acid sequence having 90% or more identity with the amino acid sequence ELKLIFLHRLKRLRKRLKRK.
[4] The peptide according to any one of the above [1] to [3], wherein the peptide is amidated at the C-terminus.
[5] The peptide according to any one of the above [1] to [4], wherein the peptide is acetylated at the N-terminus.
[6] An immunostimulant containing the peptide according to any one of the above [1] to [5].
[7] The immunostimulant according to the above [6], wherein the immunostimulant is a vaccine adjuvant.
[8] A vaccine composition containing the peptide according to any one of the above [1] to [5] and at least one antigen.
[9] A hair grower containing the peptide according to any one of the above [1] to [5].
[10] A method for immunostimulation, comprising administering an effective amount of the peptide according to any one of the above [1] to [5] to a mammal.
[11] A method for enhancing immunogenicity of a vaccine antigen, the method comprising administering an effective amount of the peptide according to any one of the above [1] to [5] to a mammal.

[12] The peptide according to any one of the above [1] to [5] for use in stimulation of immune responses.
[13] The peptide according to any one of the above [1] to [5] for use in enhancement of immunogenicity of a vaccine antigen.
[14] Use of the peptide according to any one of the above [1] to [5] for production of an immunostimulant, a vaccine adjuvant or a vaccine composition.
[15] A method for promoting hair growth or regrowth, comprising administering an effective amount of the peptide according to any one of the above [1] to [5] to a mammal.
[16] The peptide according to any one of the above [1] to [5] for use in promotion of hair growth or regrowth.
[17] Use of the peptide according to any one of the above [1] to [5] for production of a hair grower.

Advantageous Effects of Invention

The present invention provides a novel peptide. The novel peptide of the present invention has immunostimulatory effect and hair growth and/or regrowth promoting effect. The novel peptide of the present invention is considerably more effective for immunostimulation than its analogous peptides described in prior patent documents etc. The present invention also provides a novel immunostimulant, a novel vaccine adjuvant, a novel vaccine composition and a novel hair grower each of which contains the peptide.

The peptide of the present invention is effective for inducing the production of cytokines, inducing the expression of T-cell costimulatory molecules, and activating inflammasomes, and is useful as an immunostimulant. The peptide of the present invention is also effective for enhancing the immunogenicity of a vaccine antigen, and is particularly useful as a vaccine adjuvant. The vaccine adjuvant containing the peptide of the present invention can be used as an efficient adjuvant in vaccine therapies for infections, cancers, lifestyle-related diseases, etc. Moreover, the peptide of the present invention, which is a short-chain peptide of 23 or less amino acid residues, can advantageously be mass produced at low cost because highly efficient synthesis methods and analysis methods for short-chain peptides have already been established.

The peptide of the present invention is effective for proliferating hair follicle dermal papilla cells and promoting the production of growth factors for hair follicle dermal papilla cells, and is useful as a hair grower, a hair regrowth promoter, etc. The present inventors made modifications to AG30, which consists of 30 amino acid residues, and thereby produced various peptides. As a result, they found that the peptide of the present invention is considerably more active for proliferating hair follicle dermal papilla cells and promoting the production of growth factors for hair follicle dermal papilla cells. Moreover, the peptide of the present invention used as an active ingredient, which is a short-chain peptide of 23 or less amino acid residues, can advantageously be mass produced at low cost because highly efficient synthesis methods and analysis methods for short-chain peptides have already been established.

DESCRIPTION OF EMBODIMENTS

Peptide

Figure 1:
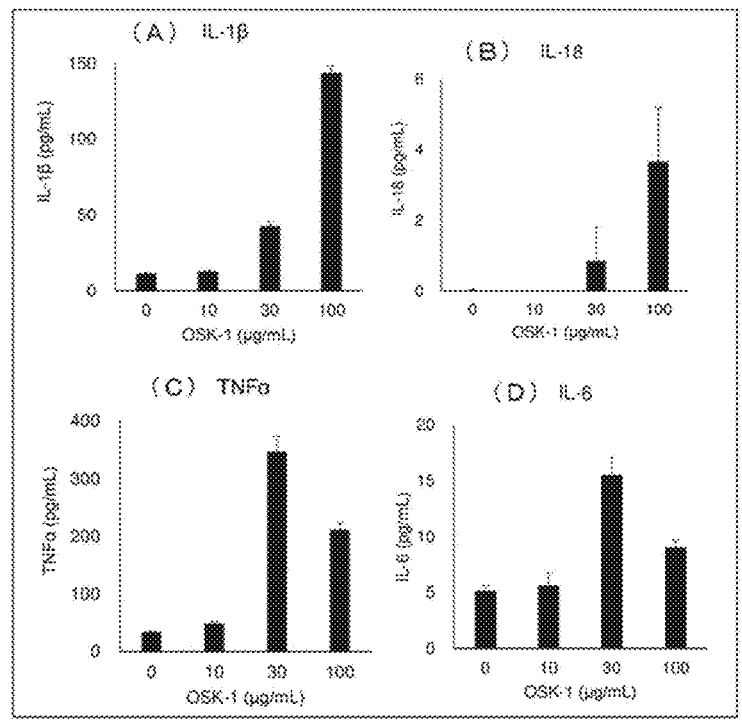
FIG. 1 shows the results of the measurement of the cytokine concentrations in the culture supernatant of the LPS-primed THP-1 cells cultured in the presence of OSK-1. Panel A shows the results of IL-1β, panel B shows the results of IL-18, panel C shows the results of TNFα, and panel D shows the results of IL-6.
Figure 2:
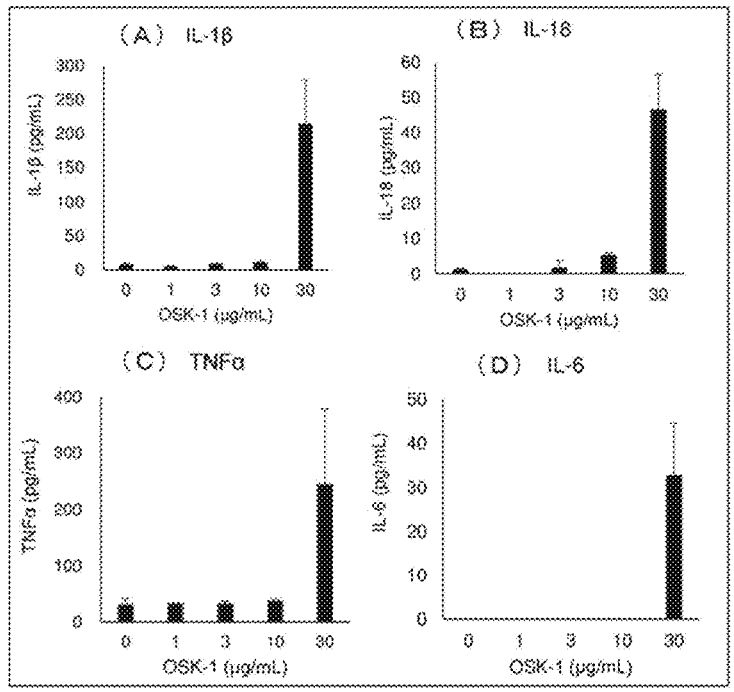
FIG. 2 shows the results of the measurement of the cytokine concentrations in the culture supernatant of the PMA-differentiated THP-1 cells cultured in the presence of OSK-1. Panel A shows the results of IL-1β, panel B shows the results of IL-18, panel C shows the results of TNFα, and panel D shows the results of IL-6.

The present invention provides a peptide of 23 or less amino acids comprising the amino acid sequence LHRLKRLRKRL (SEQ ID NO: 1) (hereinafter also called simply "the peptide of the present invention"). The peptide of the present invention comprises the amino acid sequence represented by SEQ ID NO: 1.

The peptide of the present invention is a peptide consisting of the amino acid sequence represented by SEQ ID NO: 1, or a peptide consisting of the amino acid sequence represented by SEQ ID NO: 1 and one or more additional amino acids attached to the N-terminus and/or the C-terminus of the amino acid sequence represented by SEQ ID NO: 1. The peptide of the present invention may comprise an amino acid sequence consisting of the amino acid sequence represented by SEQ ID NO: 1 and an additional amino acid residue(s) such as F, IF, LIF, KLIF, LKLIF, ELKLIF, etc. attached to the N-terminus of the amino acid sequence represented by SEQ ID NO: 1. The peptide of the present invention may comprise an amino acid sequence consisting of the amino acid sequence represented by SEQ ID NO: 1 and an additional amino acid residue(s) such as K, KR, KRK, KRKL, KRKLR, KRKLRL, KRKLRLW, KRKLRLWH, KRKLRLWHR, KRKLRLWHRK, KRKLRLWHRKR, KRKLRLWHRKRY, etc. attached to the C-terminus of the amino acid sequence represented by SEQ ID NO: 1.

The peptide of the present invention is preferably a peptide of 23 or less amino acids comprising an amino acid sequence consisting of the amino acid sequence represented by SEQ ID NO: 1 and an additional residue K attached to the C-terminus of the amino acid sequence represented by SEQ ID NO: 1, namely, the amino acid sequence LHRLKRLRKRLK (SEQ ID NO: 9). More preferably, the residue K at the C-terminus of the amino acid sequence represented by SEQ ID NO: 9 is an L-isomer.

The peptide of the present invention is more preferably a peptide of 23 or less amino acids comprising the amino acid sequence LHRLKRLRKRL (SEQ ID NO: 1), wherein the peptide comprises the amino acid sequence ELKLIFLHRLKRLRKRLKRK (SEQ ID NO: 2) or an amino acid sequence having 90% or more, preferably 95% or more identity with the amino acid sequence ELKLIFLHRLKRLRKRLKRK. Preferable examples of such a peptide include a peptide consisting of the amino acid sequence represented by SEQ ID NO: 2, 3 or 6, and a peptide comprising any of these sequences.

The peptide of the present invention is more preferably a peptide of 23 or less amino acids comprising the amino acid sequence represented by SEQ ID NO: 1, wherein the 23 or less amino acids are from the amino acid sequence ELKLIFLHRLKRLRKRLKRKLRLWHRKRY (SEQ ID NO: 14).

The number of amino acids in the peptide of the present invention may be at least 11, 12, 13, 14, 15, 16, 17, 18, 19, 20, 21, 22 or 23. The number of amino acids in the peptide of the present invention may be up to 23, 22, 21, 20, 19, 18, 17, 16, 15, 14, 13, 12 or 11.

The residue(s) "L", "RL" or "KRL" at the C-terminus of the amino acid sequence LHRLKRLRKRL (SEQ ID NO: 1) greatly affects the immunostimulatory effect or the hair growth effect of the peptide of the present invention.

The residue "L" at the N-terminus of the amino acid sequence LHRLKRLRKRL (SEQ ID NO: 1) greatly affects the immunostimulatory effect or the hair growth effect of the peptide of the present invention.

The peptide of the present invention is more preferably a peptide comprising the amino acid sequence ELKLIFLHRLKRLRKRLKRK (SEQ ID NO: 2), ELKLIFLHRLKRLRKRLK (SEQ ID NO: 3), LKLIFLHRLKRLRKRLKR (SEQ ID NO: 6), KLIFLHRLKRLRKRLK (SEQ ID NO: 7), LIFLHRLKRLRKRL (SEQ ID NO: 8), FLHRLKRLRKRL (SEQ ID NO: 10) or the like.

In particular, a peptide consisting of the amino acid sequence ELKLIFLHRLKRLRKRLKRK (SEQ ID NO: 2), ELKLIFLHRLKRLRKRLK (SEQ ID NO: 3), LKLIFLHRLKRLRKRLKR (SEQ ID NO: 6), KLIFLHRLKRLRKRLK (SEQ ID NO: 7), LIFLHRLKRLRKRL (SEQ ID NO: 8), FLHRLKRLRKRL (SEQ ID NO: 10) or the like is preferable as the peptide of the present invention.

In particular, a peptide consisting of the amino acid sequence ELKLIFLHRLKRLRKRLKRK (SEQ ID NO: 2), ELKLIFLHRLKRLRKRLK (SEQ ID NO: 3), LKLIFLHRLKRLRKRLKR (SEQ ID NO: 6) or KLIFLHRLKRLRKRLK (SEQ ID NO: 7) is more preferable as the peptide of the present invention.

In particular, a peptide consisting of the amino acid sequence ELKLIFLHRLKRLRKRLKRK (SEQ ID NO: 2), ELKLIFLHRLKRLRKRLK (SEQ ID NO: 3) or LKLIFLHRLKRLRKRLKR (SEQ ID NO: 6) is more preferable as the peptide of the present invention.

The C-terminus of the peptide of the present invention may be a carboxyl group (—COOH), a carboxylate (—COO−), an amide (—CONH$_2$) or an ester (—COOR). Examples of the R moiety in the ester include $C_{1-6}$ alkyl groups such as methyl, ethyl, n-propyl, isopropyl, n-butyl, etc.; $C_{3-8}$ cycloalkyl groups such as cyclopentyl, cyclohexyl, etc.; $C_{6-12}$ aryl groups such as phenyl, α-naphthyl, etc.; and $C_{7-14}$ aralkyl groups such as phenyl-$C_{1-2}$ alkyl groups including benzyl, phenethyl, etc., α-naphthyl-$C_{1-2}$ alkyl groups including α-naphthylmethyl etc., and the like. Another example can be a pivaloyloxymethyl group or the like, which is widely used as an ester for oral use. Examples of the amide moiety include amides; amides substituted with one or two $C_{1-6}$ alkyl groups; amides substituted with one or two $C_{1-6}$ alkyl groups substituted with a phenyl group; amides in which a 5- to 7-membered azacyclo alkane containing the nitrogen atom of the amide group is formed; and the like. When the peptide of the present invention has a carboxyl group or a carboxylate group in a site other than the C-terminus, these groups may be amidated or esterified. Such peptides can also be examples of the peptide of the present invention. The peptide of the present invention is preferably amidated at the C-terminus.

In the peptide of the present invention, the amino group at the N-terminus may be protected by a protecting group (for example, $C_{1-6}$ acyl groups including a formyl group, a $C_{2-6}$ alkanoyl group such as acetyl etc., and the like; and others), a glutamyl group resulting from in vivo N-terminal cleavage may be pyroglutamated, and a substituent (for example, —OH, —SH, an amino group, an imidazole group, an indole group, a guanidino group, etc.) in the side chain of an intramolecular amino acid may be protected by an appropriate protecting group (for example, $C_{1-6}$ acyl groups including a formyl group, a $C_{2-6}$ alkanoyl group such as acetyl etc., and the like; and others). Such peptides can also be examples of the peptide of the present invention. The peptide of the present invention is preferably acetylated at the N-terminus. The peptide of the present invention is more preferably acetylated at the N-terminus and amidated at the C-terminus.

The amino acids constituting the peptide of the present invention may have a substituent in the side chain. The substituent is not particularly limited and the examples include a fluorine atom, a chlorine atom, a cyano group, a hydroxyl group, a nitro group, an alkyl group, a cycloalkyl group, an alkoxy group, an amino group, a phosphate group, etc. The substituent in the side chain may be protected by a protecting group. Moreover, glycopeptides, in which a sugar chain is attached to peptides, are also examples of the peptide of the present invention.

The peptide of the present invention may be in the form of a salt, preferably a physiologically acceptable salt. Examples of the physiologically acceptable salt include salts of acids such as hydrochloric acid, sulfuric acid, lactic acid, tartaric acid, maleic acid, fumaric acid, oxalic acid, malic acid, citric acid, oleic acid, palmitic acid, nitric acid, phosphoric acid, trifluoroacetic acid, methanesulfonic acid, benzenesulfonic acid, p-toluenesulfonic acid, etc.; salts of hydroxides or carbonates of aluminum or alkali metals or alkaline earth metals, such as sodium, potassium, calcium, etc.; salts of triethylamine, benzylamine, diethanolamine, tert-butylamine, dicyclohexylamine, arginine or the like; and other salts. Particularly preferable examples are hydrochlorides, acetates and trifluoroacetates.

The peptide of the present invention may contain an unnatural amino acid as long as the peptide retains its original properties. Optionally, the peptide of the present invention may be conjugated with another substance as long as the peptide retains its original properties. Examples of the substance which can be conjugated to the peptide include lipids, sugars, sugar chains, an acetyl group, natural or synthetic polymers, etc. Optionally, the peptide of the present invention may be modified by glycosylation, side-chain oxidation, phosphorylation or the like as long as the modified peptide retains its original properties.

The peptide of the present invention can be produced by a solid phase synthesis method (e.g., the Fmoc method and the Boc method) or a liquid phase synthesis method according to a known ordinary peptide synthesis protocol. Alternatively, a transformant with an expression vector containing a DNA encoding the peptide of the present invention can be used to produce the peptide of interest. Alternatively, a peptide composed of the peptide of the present invention as part is firstly produced by a transformant with an expression vector containing a DNA encoding the former peptide, and then cleaved with an appropriate protease or peptidase to yield the peptide of interest. Alternatively, the peptide of the present invention can be produced by in vitro coupled transcription-translation system.

The peptide of the present invention is effective for inducing the production of cytokines, inducing the expression of T-cell costimulatory molecules, and activating inflammasomes, and is useful as an immunostimulant. The peptide of the present invention is particularly useful as a vaccine adjuvant. In addition, the peptide of the present invention is effective for proliferating hair follicle dermal papilla cells and promoting the production of growth factors for hair follicle dermal papilla cells, and is useful for hair growth, hair nourishment, hair regrowth promotion, etc.

Immunostimulant

The present invention provides an immunostimulant containing the above-described peptide of the present invention as an active ingredient. Preferably, a vaccine adjuvant is provided. In addition, the present invention provides a vaccine composition containing the above-described peptide of the present invention.

The immunostimulant of the present invention contains at least one of the peptides of the present invention. The immunostimulant of the present invention may further contain another active ingredient used for immunostimulation. The combined use of the peptide of the present invention and another active ingredient used for immunostimulation can be expected to additively or synergistically enhance immunostimulatory effect.

The immunostimulant of the present invention may be used alone or in combination with another drug, and is effective for treatment of various diseases. For example, a combination of the immunostimulant of the present invention and an anticancer drug can be used for treatment.

The immunostimulant of the present invention is effective, for example, for inducing the production of cytokines, inducing the expression of T-cell costimulatory molecules, and activating inflammasomes, and thus exhibits a highly immunostimulatory effect. The immunostimulant of the present invention is useful because it can activate both Th1-type and Th2-type immune responses.

Moreover, the immunostimulant of the present invention is effective for enhancing the immunogenicity of a vaccine antigen, and can preferably be used as an excellent vaccine adjuvant.

The vaccine adjuvant of the present invention contains at least one of the peptides of the present invention. The vaccine adjuvant of the present invention may further contain another adjuvant or another active ingredient used for immunostimulation. The combined use of the peptide of the present invention with another adjuvant or another active ingredient used for immunostimulation can be expected to additively or synergistically enhance adjuvant effect or immunostimulatory effect. Examples of the additional adjuvant and the additional active ingredient used for immunostimulation include alum, Freund's adjuvant (complete Freund's adjuvant and incomplete Freund's adjuvant), TLR agonists (Krestin, lipopolysaccharides, flagellin, CpG nucleotide, etc.), etc.

The vaccine adjuvant of the present invention together with a vaccine containing at least one antigen may be provided as a kit preparation in which the vaccine adjuvant and the vaccine are separately packed. The vaccine adjuvant and the vaccine in this kit preparation are to be mixed before use.

The vaccine adjuvant of the present invention can preferably be used for enhancing the immunogenicity of a vaccine, and the type of the vaccine is not limited. Examples of the vaccine include vaccines for prevention of infections, cancer vaccines, vaccines capable of inducing the immunity against disease-relating proteins produced in the living body, and other vaccines. Examples of the vaccines for prevention of infections include vaccines against infections such as influenza, polio, Japanese encephalitis, tuberculosis, human papillomavirus infection, malaria, SARS, typhoid fever, paratyphoid fever, plague, pertussis, epidemic typhus, etc. Examples of the cancer antigen or the cancer antigen peptide used for the cancer vaccines include WT1 peptide, MAGE peptide, MUC1 peptide, survivin, etc. Examples of the disease-relating proteins produced in the living body include amyloid-β, angiotensin II, DPPIV, IgE, IL-17, PD-1, PD-L1, etc. The antigen may be formed by conjugation of an epitope sequence with a carrier protein (for example, keyhole limpet hemocyanin (KLH) etc.).

The peptide used as the vaccine adjuvant is particularly preferably a peptide consisting of the amino acid sequence represented by SEQ ID NO: 2, 3, 6, 7, 8 or 10. In particular, a peptide consisting of the amino acid sequence represented by SEQ ID NO: 2, 3, 6 or 7 is more preferable, a peptide consisting of the amino acid sequence represented by SEQ ID NO: 2 or 3 is more preferable, and a peptide consisting of the amino acid sequence represented by SEQ ID NO: 2 is more preferable. Moreover, the peptide is preferably acetylated at the N-terminus and amidated at the C-terminus. The vaccine adjuvant of the present invention is less likely to cause unwanted effects such as pain, induration, etc. than conventional adjuvants such as alum and oily adjuvants.

The immunostimulant of the present invention can preferably be used also in a procedure involving in vitro activation of tissues and cells isolated from humans, other mammals, etc. for use in treatment etc. For example, in a therapeutic method which comprises isolating monocytes from a cancer patient, culturing the monocytes in a medium supplemented with growth factors for the monocytes, GM-CSF, IL-4, etc. for directed differentiation into dendritic cells, making a cancer antigen or a cancer antigen peptide internalized into the dendritic cells, and returning these cells to the living body, the immunostimulant of the present invention can be used together with the cancer antigen or the cancer antigen peptide. In this case, the immunostimulant of the present invention can be used in combination with an adjuvant or another active ingredient used for immunostimulation. Examples of the cancer antigen or the cancer antigen peptide used include WT1 peptide, MAGE peptide, MUC1 peptide, survivin, etc.

Vaccine Composition

The vaccine composition of the present invention contains at least one of the above-described peptides of the present invention and at least one antigen. The embodiments of the vaccine composition of the present invention include a preparation containing at least one of the peptides of present invention and at least one antigen, and a preparation containing a combined-form of at least one of the peptides of present invention and at least one antigen. In an embodiment of the combined-form, for example, the peptide of the present invention and the antigen are conjugated to form one polypeptide. In this embodiment of the combined-form, the antigen and the peptide of the present invention may be conjugated directly or via a spacer etc. Examples of the spacer include, but are not limited to, ε-aminocaproic acid. For linking the spacer to the peptide of the present invention or the antigen peptide, an amide bond and a disulfide bond can be used. PEG or oligopeptides can also be used as the spacer.

The antigen contained in the vaccine composition of the present invention is not particularly limited. Any antigen can preferably be used in the vaccine composition of the present invention as long as the antigen can be used for vaccines, including but not limited to the above-described vaccines for prevention of infections, cancer vaccines, vaccines capable of inducing the immunity against disease-relating proteins produced in the living body. In addition, the antigen is particularly preferably a peptide composed of an epitope sequence. The antigen may be conjugated to a carrier protein. As used herein, the antigen used for vaccines is called a "vaccine antigen".

Inducer of Production of Cytokines, Inducer of Expression of T-Cell Costimulatory Molecules, Activator of Inflammasomes The immunostimulant of the present invention is effective, for example, for inducing the production of cytokines, inducing the expression of T-cell costimulatory molecules, and activating inflammasomes, and thus exhibits a highly immunostimulatory effect. Therefore, the immunostimulant of the present invention encompasses an inducer of the production of cytokines, an inducer of the expression of T-cell costimulatory molecules, an activator of inflammasomes, etc.

The effect of the peptide of the present invention to induce the production of cytokines can be confirmed by, for example, the method described in Examples 2 and 3, etc. The effect of the peptide of the present invention to induce the expression of T-cell costimulatory molecules can be confirmed by, for example, the method described in Example 4 etc. The effect of the peptide of the present invention to activate inflammasomes can be confirmed by, for example, the method described in Examples 5 and 6, etc. The adjuvant effect of the peptide of the present invention can be confirmed by, for example, the above-mentioned methods for confirming the immunostimulatory effect (Examples 2 to 6), the method described in Examples 7 and 8, etc.

The inducer of the production of cytokines contains at least one of the peptides of present invention. The peptide used in the inducer of the production of cytokines is particularly preferably a peptide consisting of the amino acid sequence represented by SEQ ID NO: 2, 3, 6, 7, 8 or 10. In particular, a peptide consisting of the amino acid sequence represented by SEQ ID NO: 2 is more preferable. Moreover, the peptide is preferably acetylated at the N-terminus and amidated at the C-terminus.

Examples of the cytokine as used herein include IL-1β, IL-18, TNFα, IL-6, IL-8, IL-12, IFN-γ, IFN-α, IL-1β, MCP-1, MIP-1α, MIP-1β, iNOS, IL-17, IL-23, etc. Preferable examples are IL-1β, IL-18, TNFα, IL-6, etc.

The inducer of the expression of T-cell costimulatory molecules contains at least one of the peptides of present invention. The peptide used in the inducer of the expression of T-cell costimulatory molecules is particularly preferably a peptide consisting of the amino acid sequence represented by SEQ ID NO: 2, 3, 6, 7, 8 or 10. In particular, a peptide consisting of the amino acid sequence represented by SEQ ID NO: 2, 3, 6 or 7 is more preferable, and a peptide consisting of the amino acid sequence represented by SEQ ID NO: 2 or 3 is more preferable. Moreover, the peptide is preferably acetylated at the N-terminus and amidated at the C-terminus.

Examples of the T-cell costimulatory molecules as used herein include CD86, CD54, CD80, CD106, CD40, etc. Preferable examples are CD86, CD54, etc.

The activator of inflammasomes contains at least one of the peptides of present invention. The peptide used in the activator of inflammasomes is particularly preferably a peptide consisting of the amino acid sequence represented by SEQ ID NO: 2, 3, 6, 7, 8 or 10. In particular, a peptide consisting of the amino acid sequence represented by SEQ ID NO: 2 is more preferable. Moreover, the peptide is preferably acetylated at the N-terminus and amidated at the C-terminus.

The immunosuppressant, the vaccine adjuvant and the vaccine composition of the present invention can be prepared in a dosage form from the above-described peptide of the present invention blended with a pharmaceutically acceptable carrier or additive as appropriate. Specific examples of the dosage form include oral preparations such as tablets (including sugar-coated tablets), coated tablets, pills, powders, granules, capsules, solutions, suspensions, emulsions, etc.; and parenteral preparations such as injectable preparations (e.g., subcutaneous injectable preparations, intravenous injectable preparations, intramuscular injectable preparations, intraperitoneal injectable preparations, etc.), infusions, intravenous infusions, external preparations (e.g., transnasal preparations, transdermal preparations, ointments, etc.), suppositories (e.g., rectal suppositories, vaginal suppositories, etc.), ointments, patches, solutions, etc.

Oral solid preparations (tablets, pills, capsules, powders, granules, etc.) can be produced by mixing an active ingredient with a filler (lactose, mannitol, glucose, microcrystalline cellulose, starch, etc.), a binder (hydroxypropyl cellulose, polyvinylpyrrolidone, magnesium aluminometasilicate, etc.), a disintegrant (calcium carboxymethyl cellulose etc.), a lubricant (magnesium stearate etc.), a stabilizer, a solubilizer (glutamic acid, aspartic acid, etc.) and/or the like, and processing the mixture into a dosage form of interest in the usual manner. If needed, the oral solid preparations may be covered with a coating material (sucrose, gelatin, hydroxypropyl cellulose, hydroxypropyl methylcellulose phthalate, etc.) or with two or more coating layers.

Oral liquid preparations (solutions, suspensions, emulsions, syrups, elixirs, etc.) can be produced by dissolving, suspending or emulsifying an active ingredient in a commonly used diluent (purified water, ethanol, a mixture of them, etc.). The oral liquid preparations may further contain a wetting agent, a suspending agent, an emulsifier, a sweetener, a flavoring agent, a fragrance, a preservative, a buffering agent and/or the like.

The parenteral preparations are, for example, external preparations for skin. The external preparations for skin can be in the form of solutions, creams, ointments, gels, aerosols or the like, but are not limited thereto. Other forms suitable for external use may also be employed.

As needed, the external preparations for skin can contain water, a lower alcohol, a solubilizer, a surfactant, an emulsion stabilizer, a gelatinizing agent, an adhesive and/or other ingredients including a commonly used base appropriate for the desired dosage form. Further, a vasodilator, a corticosteroid, a moisturizer, a microbicide, a refrigerant, a vitamin, a fragrance, a pigment and/or the like can be added as appropriate according to the intended use unless it impairs the effects of the present invention.

Other examples of the parenteral preparations can be injectable preparations. The injectable preparations include solutions, suspensions, emulsions, and solid preparations for injection, which are to be dissolved or suspended in a solvent before use. The injectable preparations can be produced by dissolving, suspending or emulsifying an active ingredient in a solvent. Examples of the solvent include distilled water for injection, physiological saline, vegetable oils, alcohols such as propylene glycol, polyethylene glycols, ethanol, etc., and the like, and a combination thereof. The injectable preparations may further contain a stabilizer, a solubilizer (glutamic acid, aspartic acid, polysorbate 80 (registered trademark), etc.), a suspending agent, an emulsifier, a soothing agent, a buffering agent, a preservative and/or the like. The injectable preparations are sterilized in the final step of the production process or produced in an aseptic manner. Alternatively, sterile solid preparations, for example, lyophilized preparations may be produced for use as injectable preparations. Such sterile solid preparations are to be dissolved in a sterilized or aseptic distilled water for injection or another solvent before use.

The percentage of the carrier or the additive added when the immunostimulant, the vaccine adjuvant and the vaccine composition of the present invention are prepared in a dosage form is determined as appropriate based on the range of the percentage conventionally adopted in the pharmaceutical field. The carrier or the additive that can be added is not particularly limited, and the examples include various carriers such as water, physiological saline, other aqueous solvents, aqueous or oily bases, etc.; and various additives such as fillers, binders, pH adjusters, disintegrants, absorption enhancers, lubricants, colorants, corrigents, fragrances, etc.

Examples of the additive that can be contained in tablets, capsules and the like include binders such as gelatin, cornstarch, tragacanth, gum arabic, etc.; fillers such as crystalline cellulose etc.; bulking agents such as cornstarch, gelatin, alginic acid, etc.; lubricants such as magnesium stearate etc.; sweeteners such as sucrose, lactose, saccharin, etc.; flavors such as peppermint, *Gaultheria adenothrix* oil, cherry, etc.; and the like. In the case where the unit dosage form is a capsule, a liquid carrier such as fats and oils etc. can be further contained in addition to the above-mentioned ingredients. A sterile composition for injection can be prepared according to the usual pharmaceutical formulation practice, for example, by dissolving or suspending an active ingredient in a solvent such as water for injection, a natural vegetable oil, etc. As an aqueous liquid for injection, for example, physiological saline, an isotonic solution containing glucose and an auxiliary substance (e.g., D-sorbitol, D-mannitol, sodium chloride, etc.), or the like can be used, optionally together with a suitable solubilizer such as alcohols (e.g., ethanol etc.), polyalcohols (e.g., propylene glycol, polyethylene glycol, etc.), nonionic surfactants (e.g., polysorbate 80™, HCO-50, etc.), etc. As an oily liquid, for example, sesame oil, soybean oil or the like can be used, optionally together with a solubilizer such as benzyl benzoate, benzyl alcohol, etc. Further, a buffering agent (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant and/or the like may also be added.

The pharmaceutical preparation that can be obtained in the above manner can be administered to, for example, humans and other mammals (e.g., rats, mice, rabbits, sheep, pigs, cattle, cats, dogs, monkeys, etc.).

The dose varies depending on the subject, the target disease, the administration route and the like. For example, in the case of oral administration, the daily dose for an adult human weighing 60 kg is typically about 0.1 to 100 mg, preferably about 1.0 to 50 mg, and more preferably about 1.0 to 20 mg in terms of the active ingredient. In the case of parenteral administration, for example, in the form of an injectable preparation, the daily intravenous dose for an adult human weighing 60 kg is typically about 0.01 to 30 mg, preferably about 0.1 to 20 mg, and more preferably about 0.1 to 10 mg in terms of the active ingredient. The total daily dose may be given as a single dose or in divided doses.

Examples of the administration method of the immunostimulant, the vaccine adjuvant and the vaccine composition of the present invention include transdermal administration, transmucosal administration, oral administration, subcutaneous injection, intracutaneous injection, intramuscular injection, etc. More preferable examples are intracutaneous injection and intramuscular injection. In the case where the vaccine adjuvant of the present invention and a vaccine antigen are administered in combination, the administration of the vaccine antigen may be concomitant with, preceded by or followed by the administration of the vaccine adjuvant of the present invention.

Hair Grower

The present invention provides a hair grower containing the above-described peptide of the present invention as an active ingredient. The hair grower of the present invention is effective, for example, for proliferating hair follicle dermal papilla cells, promoting the production of growth factors for hair follicle dermal papilla cells, nourishing hair, promoting hair regrowth, regrowing hair, and increasing hair volume, and thus exhibits an excellent hair-growth effect. Therefore, the hair grower of the present invention can also be referred to as an agent for proliferating hair follicle dermal papilla cells, an agent for promoting the production of growth factors for hair follicle dermal papilla cells, an agent for nourishing hair, an agent for promoting hair regrowth, an agent for regrowing hair, an agent for increasing hair volume, etc. The hair grower of the present invention can be provided in the form of cosmetics, quasi drugs, medicinal drugs, foods and drinks, dietary supplements or the like.

The hair grower, the agent for proliferating hair follicle dermal papilla cells, the agent for promoting the production of growth factors for hair follicle dermal papilla cells, the agent for nourishing hair, the agent for promoting hair regrowth, the agent for regrowing hair or the agent for increasing hair volume contains at least one of the peptides of the present invention. The peptide used in the hair grower or the like is particularly preferably a peptide consisting of the amino acid sequence represented by SEQ ID NO: 2, 3, 6, 7 or 8. In particular, a peptide consisting of the amino acid sequence represented by SEQ ID NO: 2, 3, 6 or 7 is more preferable, a peptide consisting of the amino acid sequence represented by SEQ ID NO: 2, 3 or 6 is more preferable, a peptide consisting of the amino acid sequence represented by SEQ ID NO: 2 or 3 is more preferable, and a peptide consisting of the amino acid sequence represented by SEQ ID NO: 2 is more preferable. Moreover, the peptide is preferably acetylated at the N-terminus and amidated at the C-terminus.

Examples of the growth factor as used herein include KGF (keratinocyte growth factor), HGF (hepatocyte growth factor), VEGF (vascular endothelial growth factor), IGF (insulin growth factor), EGF (epithelial growth factor), FGF (fibroblast growth factor), PDGF (platelet-derived growth factor), TGF β1 (transforming growth factor β1), etc. Preferable examples are KGF, HGF, VEGF, etc.

In an embodiment where the hair grower of the present invention is in the form of cosmetics or quasi drugs, the form of cosmetics or quasi drugs is not particularly limited. Examples of the form of cosmetics or quasi drugs include external preparations for skin, shampoos, conditioners, treatments, hair care products and hair styling products.

In the embodiment where the hair grower of the present invention is in the form of cosmetics or quasi drugs, the peptide of the present invention can be blended with ingredients generally used in cosmetics or quasi drugs as appropriate according to the purpose. Examples of such ingredients include oils, wetting agents, moisturizers, emulsifiers, ultraviolet absorbers, surfactants, antioxidants, stabilizers, solubilizers, thickeners, fillers, chelators, sunscreens, defoamants, emollients, colorants, preservatives, propellants, acidifying or alkalinizing agents, silicones, vitamins, dyes, pigments, nano pigments, fragrances, organic solvents such as alcohols etc., water and the like.

Preferable examples of the form of cosmetics or quasi drugs include external preparations for skin. The external preparations for skin can be in the form of solutions, creams, ointments, gels, aerosols or the like, but are not limited thereto. Other forms suitable for external use may also be employed.

As needed, the external preparations for skin can contain water, a lower alcohol, a solubilizer, a surfactant, an emulsion stabilizer, a gelatinizing agent, an adhesive and/or other ingredients including a commonly used base appropriate for the desired dosage form. Further, a vasodilator, a corticosteroid, a moisturizer, a microbicide, a refrigerant, a vitamin, a fragrance, a pigment and/or the like can be added as appropriate according to the intended use unless it impairs the effects of the present invention.

In an embodiment where the hair grower of the present invention is in the form of medicinal drugs, the hair grower can be prepared in a dosage form from the above-described peptide of the present invention, namely an active ingredient, blended with a pharmaceutically acceptable carrier or additive as appropriate. The dosage form is not particularly limited, and the examples include oral preparations such as tablets (including sugar-coated tablets), coated tablets, pills, powders, granules, capsules, solutions, suspensions, emulsions, etc.; and parenteral preparations such as injectable preparations (e.g., subcutaneous injectable preparations, intravenous injectable preparations, intramuscular injectable preparations, intraperitoneal injectable preparations, etc.), infusions, intravenous infusions, external preparations (e.g., transnasal preparations, transdermal preparations, ointments, etc.), suppositories (e.g., rectal suppositories, vaginal suppositories, etc.), ointments, patches, solutions, etc. Preferable examples are external preparations.

The parenteral preparations are, for example, external preparations for skin. The external preparations for skin can be in the form of solutions, creams, ointments, gels, aerosols or the like, but are not limited thereto. Other forms suitable for external use may also be employed.

As needed, the external preparations for skin can contain water, a lower alcohol, a solubilizer, a surfactant, an emulsion stabilizer, a gelatinizing agent, an adhesive and/or other ingredients including a commonly used base appropriate for the desired dosage form. Further, a vasodilator, a corticosteroid, a moisturizer, a microbicide, a refrigerant, a vitamin, a fragrance, a pigment and/or the like can be added as appropriate according to the intended use unless it impairs the effects of the present invention.

Oral solid preparations (tablets, pills, capsules, powders, granules, etc.) can be produced by mixing an active ingredient with a filler (lactose, mannitol, glucose, microcrystalline cellulose, starch, etc.), a binder (hydroxypropyl cellulose, polyvinylpyrrolidone, magnesium aluminometasilicate, etc.), a disintegrant (calcium carboxymethyl cellulose etc.), a lubricant (magnesium stearate etc.), a stabilizer, a solubilizer (glutamic acid, aspartic acid, etc.) and/or the like, and processing the mixture into a dosage form of interest in the usual manner. If needed, the oral solid preparations may be covered with a coating material (sucrose, gelatin, hydroxypropyl cellulose, hydroxypropyl methylcellulose phthalate, etc.) or with two or more coating layers.

Oral liquid preparations (solutions, suspensions, emulsions, syrups, elixirs, etc.) can be produced by dissolving, suspending or emulsifying an active ingredient in a commonly used diluent (purified water, ethanol, a mixture of them, etc.). The oral liquid preparations may further contain a wetting agent, a suspending agent, an emulsifier, a sweetener, a flavoring agent, a fragrance, a preservative, a buffering agent and/or the like.

Other examples of the parenteral preparations can be injectable preparations. The injectable preparations include solutions, suspensions, emulsions, and solid preparations for injection, which are to be dissolved or suspended in a solvent before use. The injectable preparations can be produced by dissolving, suspending or emulsifying an active ingredient in a solvent. Examples of the solvent include distilled water for injection, physiological saline, vegetable oils, alcohols such as propylene glycol, polyethylene glycols, ethanol, etc., and the like, and a combination thereof. The injectable preparations may further contain a stabilizer, a solubilizer (glutamic acid, aspartic acid, polysorbate 80 (registered trademark), etc.), a suspending agent, an emulsifier, a soothing agent, a buffering agent, a preservative and/or the like. The injectable preparations are sterilized in the final step of the production process or produced in an aseptic manner. Alternatively, sterile solid preparations, for example, lyophilized preparations may be produced for use as injectable preparations. Such sterile solid preparations are to be dissolved in a sterilized or aseptic distilled water for injection or another solvent before use.

The percentage of the carrier or the additive added when the medicinal drugs of the present invention are prepared in a dosage form is determined as appropriate based on the range of the percentage conventionally adopted in the pharmaceutical field. The carrier or the additive that can be added is not particularly limited, and the examples include various carriers such as water, physiological saline, other aqueous solvents, aqueous or oily bases, etc.; and various additives such as fillers, binders, pH adjusters, disintegrants, absorption enhancers, lubricants, colorants, corrigents, fragrances, etc.

Examples of the additive that can be contained in tablets, capsules and the like include binders such as gelatin, cornstarch, tragacanth, gum arabic, etc.; fillers such as crystalline cellulose etc.; bulking agents such as cornstarch, gelatin, alginic acid, etc.; lubricants such as magnesium stearate etc.; sweeteners such as sucrose, lactose, saccharin, etc.; flavors such as peppermint, *Gaultheria adenothrix* oil, cherry, etc.; and the like. In the case where the unit dosage form is a capsule, a liquid carrier such as fats and oils etc. can be further contained in addition to the above-mentioned ingredients. A sterile composition for injection can be prepared according to the usual pharmaceutical formulation practice, for example, by dissolving or suspending an active ingredient in a solvent such as water for injection, a natural vegetable oil, etc. As an aqueous liquid for injection, for example, physiological saline, an isotonic solution containing glucose and an auxiliary substance (e.g., D-sorbitol, D-mannitol, sodium chloride, etc.), or the like can be used, optionally together with a suitable solubilizer such as alcohols (e.g., ethanol etc.), polyalcohols (e.g., propylene glycol, polyethylene glycol, etc.), nonionic surfactants (e.g., polysorbate 80™, HCO-50, etc.), etc. As an oily liquid, for example, sesame oil, soybean oil or the like can be used, optionally together with a solubilizer such as benzyl benzoate, benzyl alcohol, etc. Further, a buffering agent (e.g., phosphate buffer, sodium acetate buffer, etc.), a soothing agent (e.g., benzalkonium chloride, procaine hydrochloride, etc.), a stabilizer (e.g., human serum albumin, polyethylene glycol, etc.), a preservative (e.g., benzyl alcohol, phenol, etc.), an antioxidant and/or the like may also be added.

The pharmaceutical preparation that can be obtained in the above manner can be administered to, for example, humans and other mammals (e.g., rats, mice, rabbits, sheep, pigs, cattle, cats, dogs, monkeys, etc.).

The dose varies depending on the subject, the target disease, the administration route and the like. For example, in the case of administration in the form of an external preparation for skin, the daily dose for an adult human weighing 60 kg is typically about 0.01 to 30 mg, preferably about 0.1 to 20 mg, and more preferably about 0.1 to 10 mg in terms of the active ingredient. In the case of oral administration, the daily dose for an adult human weighing 60 kg is typically about 0.1 to 100 mg, preferably about 1.0 to 50 mg, and more preferably about 1.0 to 20 mg in terms of the active ingredient. In the case of parenteral administration, for example, in the form of an injectable preparation, the daily intravenous dose for an adult human weighing 60 kg is typically about 0.01 to 30 mg, preferably about 0.1 to 20 mg, and more preferably about 0.1 to 10 mg in terms of the active ingredient. The total daily dose may be given as a single dose or in divided doses.

In an embodiment where the hair grower of the present invention is in the form of foods and drinks, examples of the foods and drinks include health foods, functional foods, foods for specified health use, foods for the sick, food additives, etc. The form of foods and drinks is not particularly limited. The examples include drinks such as tea drink, soft drink, carbonated drink, nutritional drink, fruit juice, lactic drink, etc.; noodles such as buckwheat noodle, wheat noodle, Chinese noodle, instant noodle, etc.; sweets and bakery such as hard candy, candy, gum, chocolate, snack, biscuit, jelly, jam, cream, baked sweets, bread, etc.; processed fishery and livestock products such as fish cake, ham, sausage, etc.; dairy products such as processed milk, fermented milk, etc.; fats, oils and processed fat and oil products such as vegetable oil, tempura oil, margarine, mayonnaise, shortening, whipped cream, dressing, etc.; seasonings such as sauce, dipping sauce, etc.; retort food products such as curry, stew, rice bowl, rice porridge, rice soup, etc.; frozen desserts such as ice cream, sherbet, shaved ice, etc.; and the like.

In an embodiment where the hair grower of the present invention is in the form of dietary supplements, it can be provided in the form of tablets, granules, powders, drinkable preparations, etc.

For the production of dietary supplements, for example, an active ingredient is mixed with one or more auxiliary agents, such as sugars such as dextrin, starch, etc.; proteins such as gelatin, soybean proteins, maize proteins, etc.; amino acids such as alanine, glutamine, isoleucine, etc.; polysaccharides such as cellulose, gum arabic, etc.; fats and oils such as soybean oil, medium-chain-fatty-acid triglycerides, etc.; and the like, and the mixture is processed into a dosage form.

A combined use of the peptide of the present invention and another active ingredient used for hair growth or regrowth promotion can be expected to additively or synergistically enhance hair growth or regrowth promoting effect. Examples of the additional active ingredient used for hair growth or regrowth promotion include minoxidil, finasteride, etc.

The present invention also includes the following.

(a) Use of the above-described peptide of the present invention for production of a vaccine adjuvant, a vaccine composition, an immunostimulant or a hair grower.

(b) The above-described peptide of the present invention for use in enhancement of the immunogenicity of a vaccine antigen, in induction of the production of cytokines, in induction of the expression of T-cell costimulatory molecules, in activation of inflammasomes, in proliferation of hair follicle dermal papilla cells, or in promotion of the production of growth factors for hair follicle dermal papilla cells.

(c) A non-therapeutic method for immunostimulation or for hair growth or regrowth promotion, comprising administering an effective amount of the above-described peptide of the present invention to a mammal.

(d) A method for enhancement of immunogenicity, for immunostimulation, or for hair growth or regrowth promotion, comprising administering an effective amount of the above-described peptide of the present invention to a mammal.

(e) A method for enhancing the immunogenicity of a vaccine antigen, comprising a step of administering an effective amount of the above-described peptide of the present invention to a mammal in need of vaccine administration.

(f) A method for promoting hair growth or regrowth, comprising a step of administering an effective amount of the above-described peptide of the present invention to a mammal in need of hair growth or regrowth promotion.

EXAMPLES

Hereinafter, the present invention will be illustrated in detail by examples, but the present invention is not limited thereto.

Example 1: Peptide Synthesis

A protected peptide-bound resin was synthesized by the Fmoc method using a fully-automatic solid-phase synthesizer according to the protocol described in Solid Phase Peptide Synthesis, Pierce (1984); Fmoc Solid Synthesis: A Practical Approach, Oxford University Press (2000); The Fifth Series of Experimental Chemistry (Jikken Kagaku Kouza), vol. 16, Synthesis of Organic Compounds IV; or the like. To the protected peptide-bound resin, trifluoroacetic acid (TFA) and a scavenger (a mixture of thioanisole, ethanedithiol, phenol, triisopropylsilane, water and the like) were added, and thereby the protected peptide was cleaved from the resin and deprotected to yield the peptide of interest as a crude product. For the purification of the peptide, the crude product was applied to a reverse-phase HPLC column (ODS) and elution was performed with a gradient of 0.1% TFA-$H_2O$/$CH_3CN$. The fractions containing the peptide of interest were combined and freeze-dried, and the peptide of interest was obtained. The amino acid sequence of the synthesized peptide was confirmed with the amino acid sequencer G1000A (Hewlett Packard), PPSQ-23A (Shimadzu Corporation) or Procise cLC (ABI). The obtained peptide was subjected to N-terminal acetylation and C-terminal amidation. The sequence of the synthesized peptide is shown below.

Figure 13:
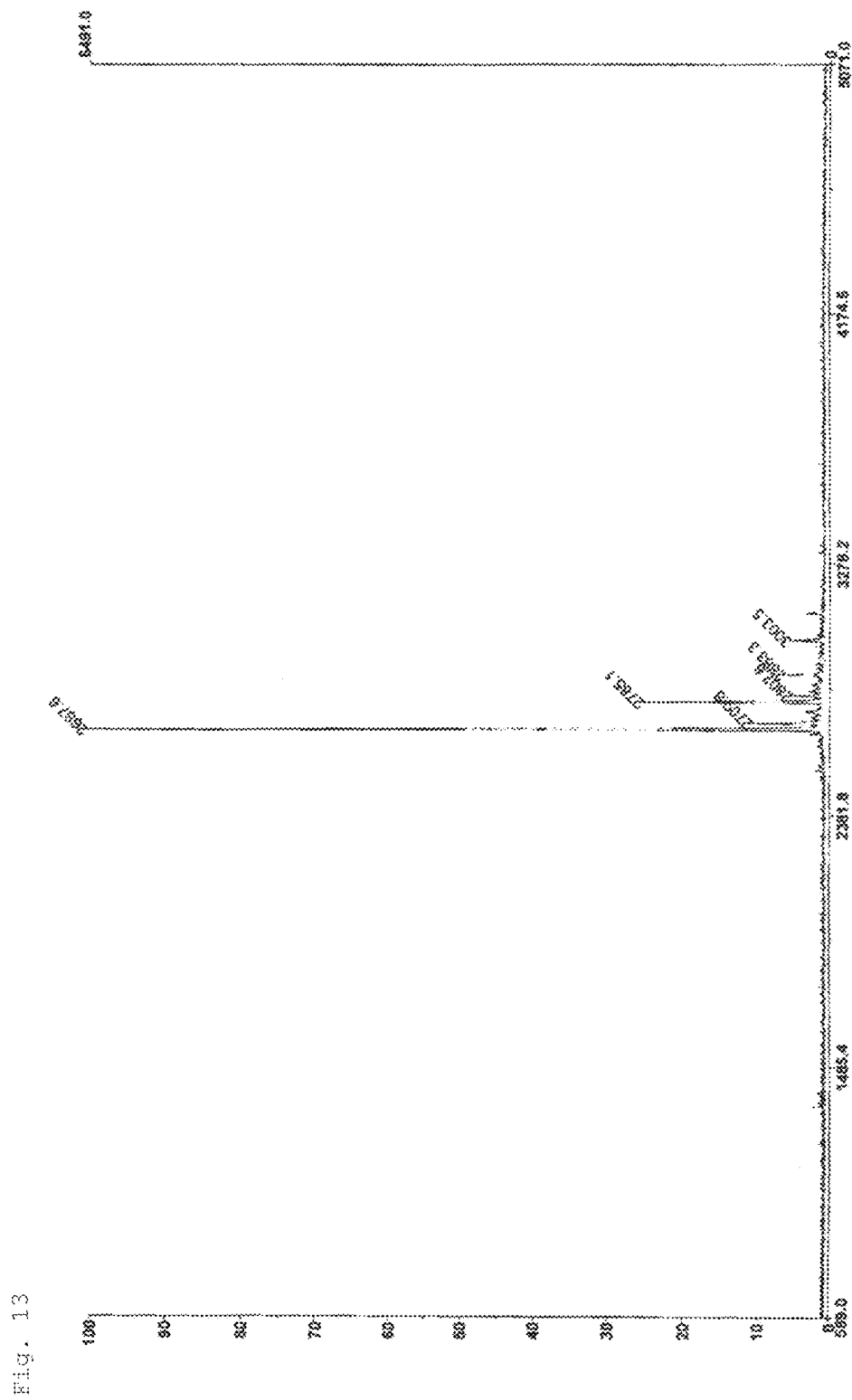
FIG. 13 shows the results of the MS analysis of OSK-1.

The molecular weight of the synthesized peptide OSK-1 was measured with a mass spectroscope (Voyager DE-Pro, serial number 6344). 0.5 μL of dihydroxybenzoic acid (DHB) as a matrix and 0.5 μL of a sample were spotted and dried. The results of the MS analysis are shown in FIG. 13.

Figure 14:
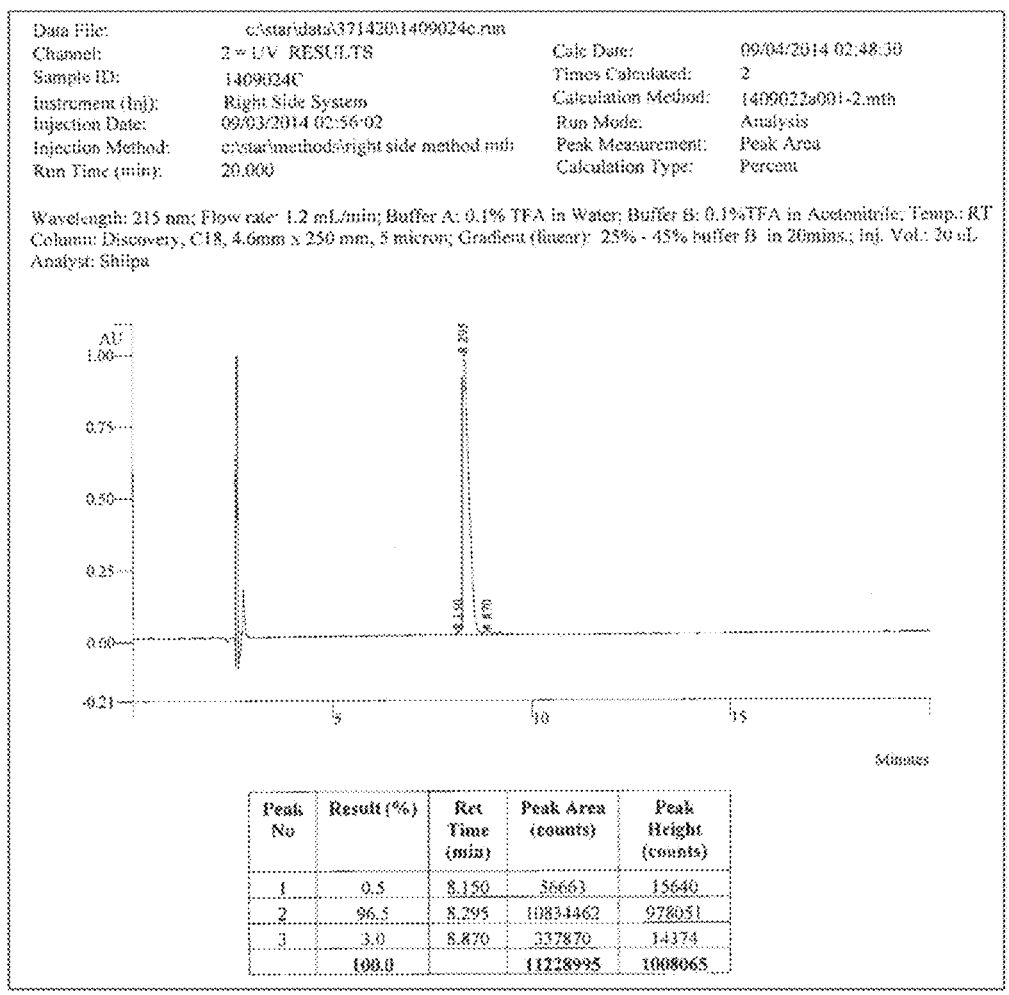
FIG. 14 shows the results of the HPLC analysis of OSK-1.
Figure 15:
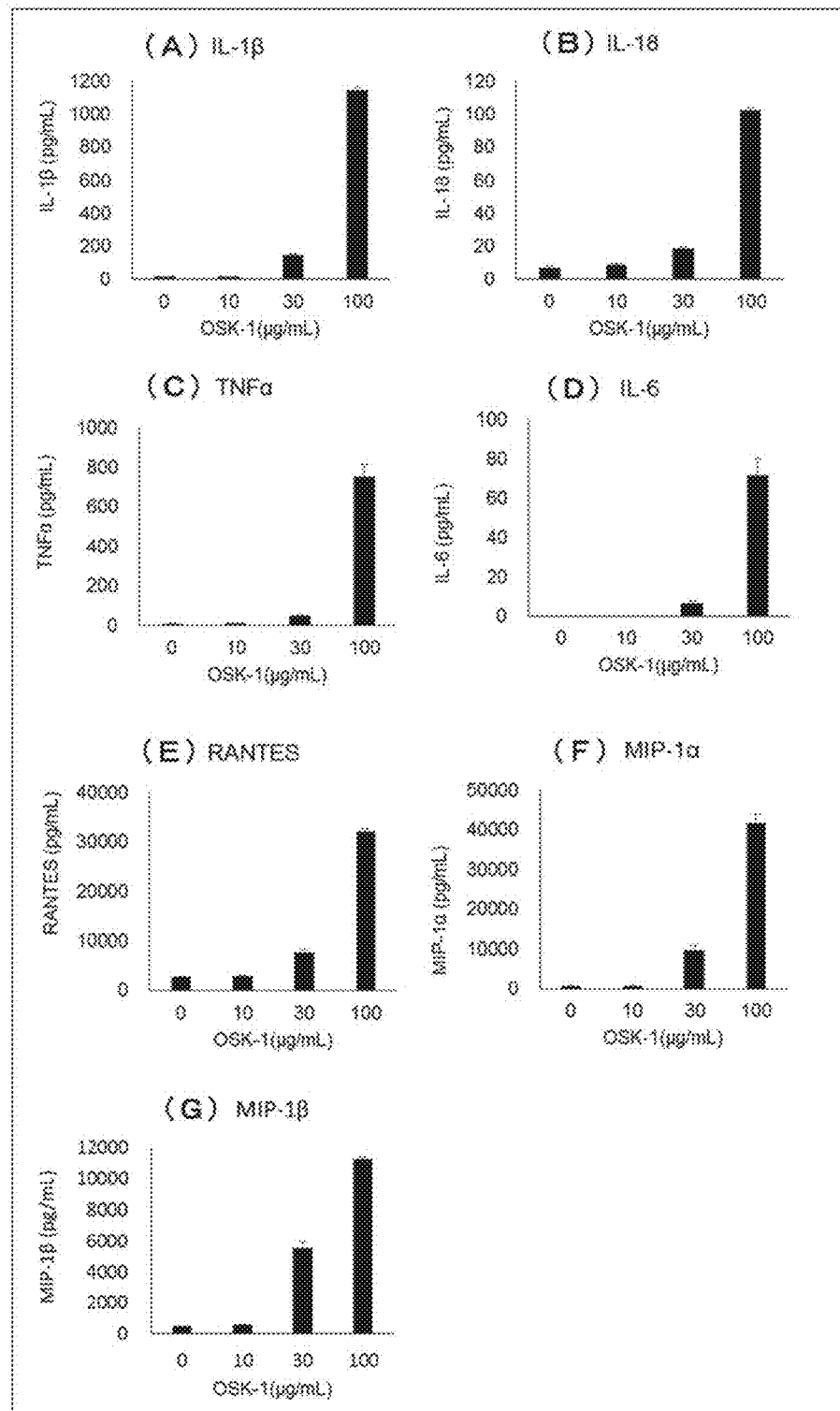
FIG. 15 shows the results of the measurement of the cytokine and chemokine concentrations in the culture supernatant of the PMA-differentiated THP-1 cells cultured in the presence of OSK-1. Panel A shows the results of IL-1β, panel B shows the results of IL-18, panel C shows the results of TNFα, panel D shows the results of IL-6, panel E shows the results of RANTES, panel F shows the results of MIP-1α, and panel G shows the results of MIP-1β.
Figure 16:
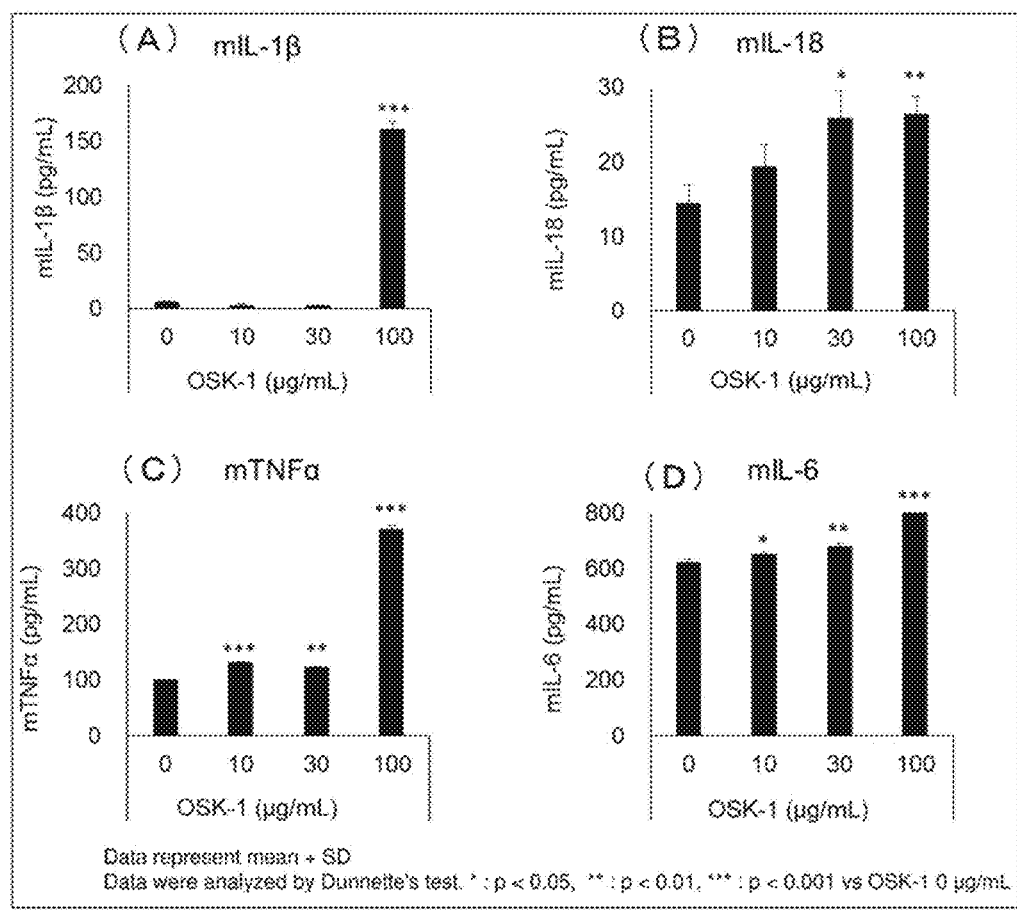
FIG. 16 shows the results of the measurement of the cytokine concentrations in the culture supernatant of the LPS-primed RAW 264.7 cells cultured in the presence of OSK-1. Panel A shows the results of IL-1β, panel B shows the results of IL-18, panel C shows the results of TNFα, and panel D shows the results of IL-6.
Figure 17:
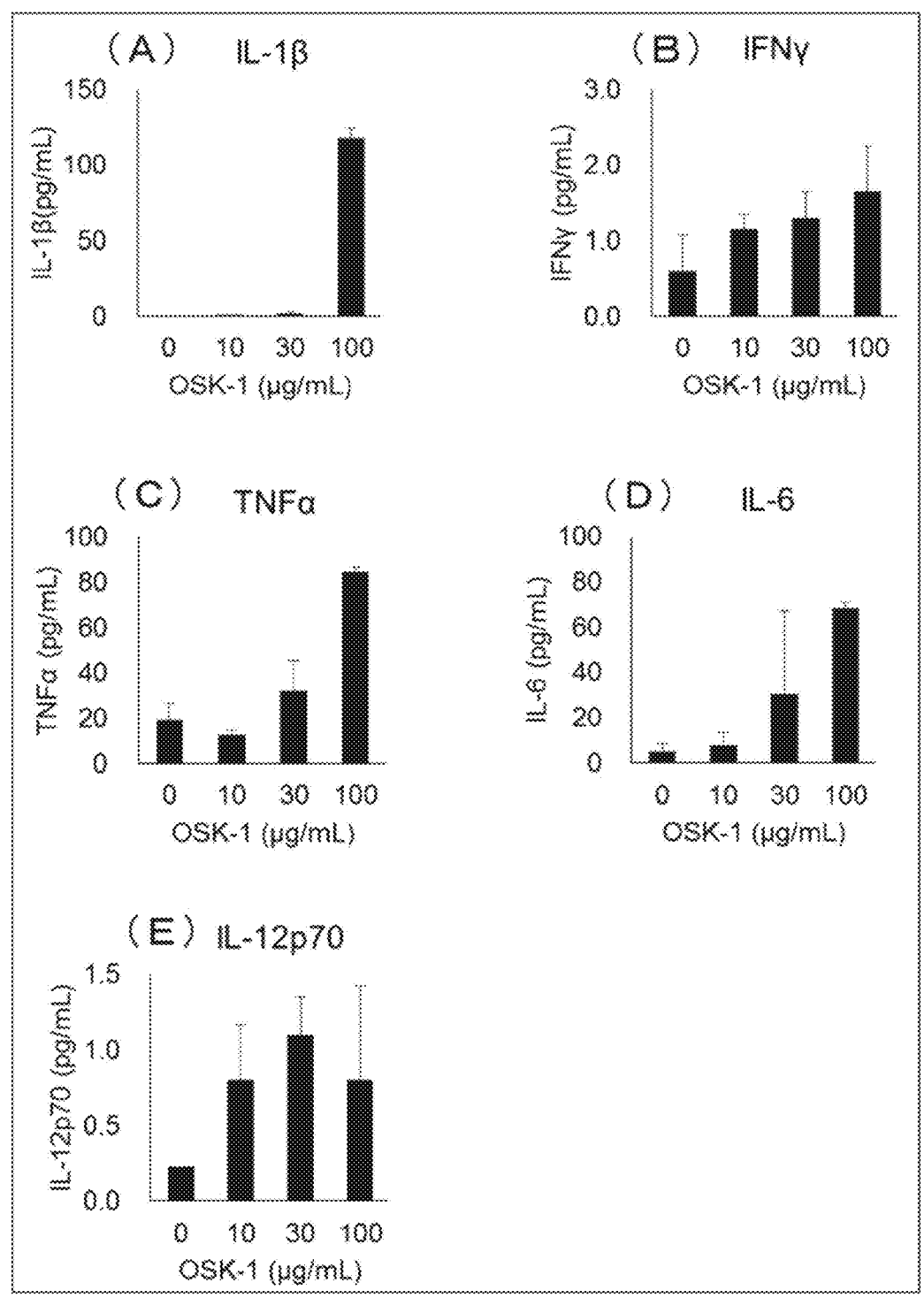
FIG. 17 shows the results of the measurement of the cytokine concentrations in the culture supernatant of the mouse bone marrow-derived dendritic cells cultured in the presence of OSK-1. Panel A shows the results of IL-1β, panel B shows the results of IFNγ, panel C shows the results of TNFα, panel D shows the results of IL-6, and panel E shows the results of IL-12p70.
Figure 18:
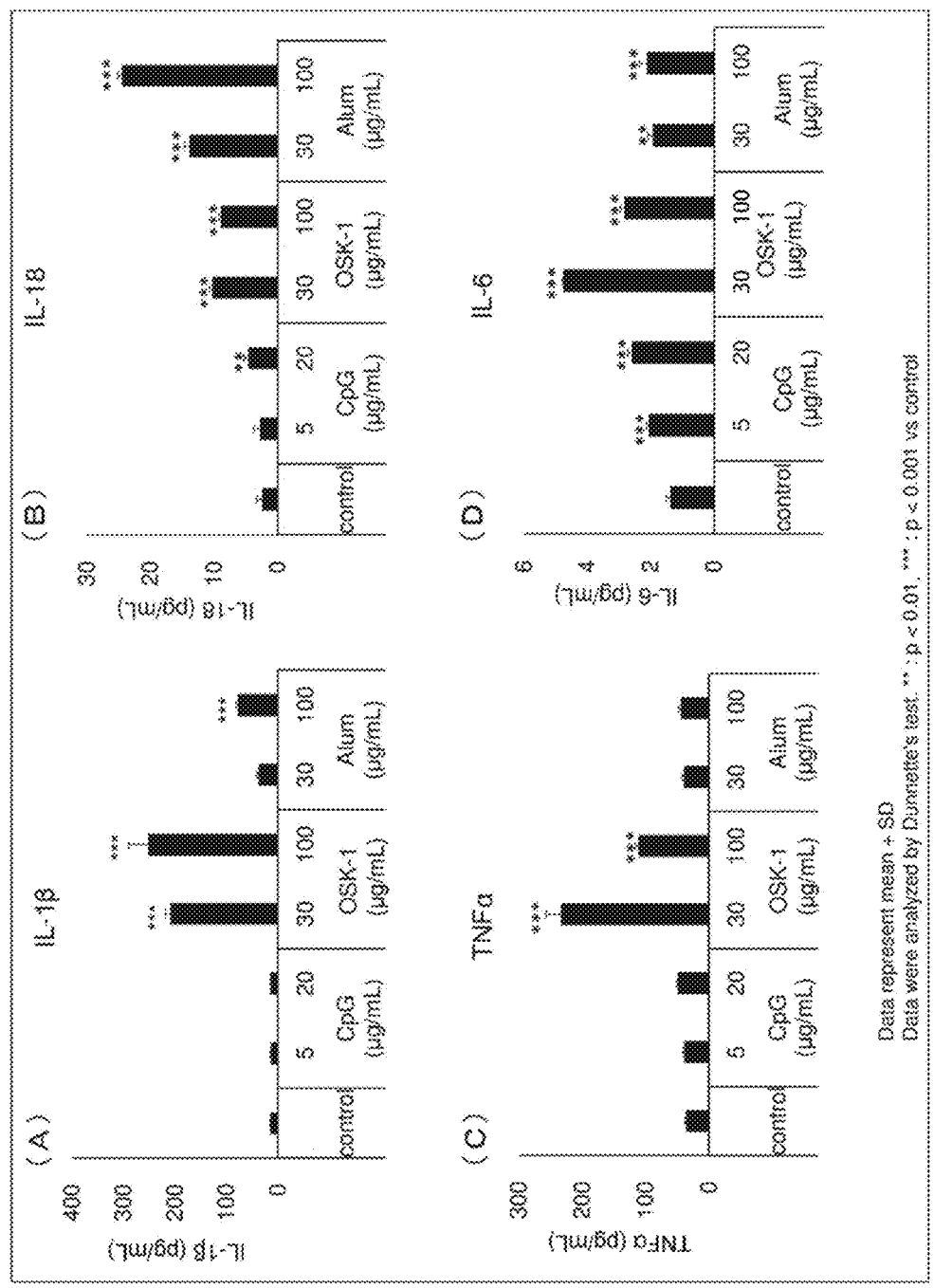
FIG. 18 shows the results of the measurement of the cytokine concentrations in the culture supernatant of the LPS-primed THP-1 cells cultured in the presence of OSK-1, alum or a CpG nucleotide. Panel A shows the results of IL-1β, panel B shows the results of IL-18, panel C shows the results of TNFα, and panel D shows the results of IL-6.

The purity of the synthesized OSK-1 was measured with an HPLC system under the following analytical conditions.
HPLC model: Waters Alliance 2690
Sample solution: 1 mg/mL aqueous solution
Injection volume: 20 μL
Measurement wavelength: 215 nm
Flow rate: 1.2 mL/min.
Column: Discovery, C18, 4.6 mm×250 mm, 5 micron
Column temperature: room temperature
Mobile phase A: 0.1% trifluoroacetic acid in water
Mobile phase B: 0.1% trifluoroacetic acid in acetonitrile
Gradient conditions: linear gradient of mobile phase B from 25% to 45% in 20 minutes (25→45% buffer B in 20 minutes)
The results of the HPLC analysis are shown in FIG. 14.

TABLE 1

| Peptide | N-terminus | 1 | 2 | 3 | 4 | 5 | 6 | 7 | 8 | 9 | 10 | 11 | 12 | 13 | 14 | 15 | 16 | 17 | 18 | 19 | 20 | SEQ ID NO: | C-terminus |
|---|---|---|---|---|---|---|---|---|---|---|---|---|---|---|---|---|---|---|---|---|---|---|---|
| OSK-1 | Acetyl | E | L | K | L | I | F | L | H | R | L | K | R | L | R | K | R | L | K | R | K | SEQ ID NO: 2 | amide |
| AAP-1 | Acetyl | E | L | K | L | I | F | L | H | R | L | K | R | L | R | K | R | L | K | | | SEQ ID NO: 3 | amide |
| AAP-4 | Acetyl | | L | K | L | I | F | L | H | R | L | K | R | L | R | K | R | L | K | R | | SEQ ID NO: 6 | amide |
| AAP-5 | Acetyl | | | K | L | I | F | L | H | R | L | K | R | L | R | K | R | L | K | | | SEQ ID NO: 7 | amide |
| AAP-6 | Acetyl | | | | L | I | F | L | H | R | L | K | R | L | R | K | R | L | | | | SEQ ID NO: 8 | amide |
| AAP-11 | Acetyl | | | | | | F | L | H | R | L | K | R | L | R | K | R | L | | | | SEQ ID NO: 10 | amide |
| AAP-2 | Acetyl | E | L | K | L | I | F | L | H | R | L | K | R | L | R | K | R | | | | | SEQ ID NO: 4 | amide |
| AAP-3 | Acetyl | E | L | K | L | I | F | L | H | R | L | K | R | L | R | | | | | | | SEQ ID NO: 5 | amide |
| AAP-12 | Acetyl | | | | | | | | H | R | L | K | R | L | R | K | R | L | K | R | K | SEQ ID NO: 11 | amide |

Example 2: Effect on Cytokine Production in Human Monocyte Cell Line (THP-1) (1)

(1) Experimental Method

Human monocyte cell line THP-1 (JCRB registration number: JCRB0112) was suspended at $1\times10^6$ cells/mL in RPMI1640 medium containing 1 μg/mL lipopolysaccharide (LPS) and 10% FBS, and incubated in a $CO_2$ incubator for 3 hours for cell priming. The cell suspension was centrifugated, the cells were resuspended at $1\times10^6$ cells/mL in RPMI1640 medium containing 10% FBS, and the cell suspension was added to a 24-well plate at 500 μL/well. An OSK-1 solution was prepared at a 2-fold higher concentration than the final concentration in RPMI1640 medium containing 10% FBS and added to the plate at 500 μL/well. After about 16 hours, the culture supernatant was harvested, and the cytokine concentrations in the supernatant were measured by ELISA.

(2) Results

The results of the measurement of the IL-1β, IL-18, TNFα and IL-6 concentrations in the culture supernatant are shown in FIGS. 1A to 1D.

The addition of OSK-1 was shown to induce the production of the cytokines in the LPS-primed THP-1 cells in an OSK-1 concentration dependent manner.

Example 3: Effect on Cytokine Production in Human Monocyte Cell Line (THP-1) (2)

(1) Experimental Method

THP-1 cells were suspended at $5\times10^3$ cells/mL in RPMI1640 medium containing 50 ng/mL PMA (phorbol 12-myristate 13-acetate) and 10% FBS, and seeded at $5\times10^5$ cells/well on a 24-well plate. The cells were cultured in a $CO_2$ incubator for 2 days for differentiation into macrophages. After the 2-day culture, the medium was removed, an OSK-1 solution in RPMI1640 medium containing 10% FBS was added to the wells, and overnight culture was performed. Sixteen hours after the addition, the culture supernatant was harvested, and the cytokine concentrations in the supernatant were measured by ELISA.

(2) Results

The results of the measurement of the IL-1β, IL-18, TNFα and IL-6 concentrations in the culture supernatant are shown in FIGS. 2A to 2D.

The addition of OSK-1 at a concentration of 30 μg/mL strongly induced the production of the cytokines in the PMA-differentiated THP-1 cells.

Example 4: Effect on CD86 and CD54 Expression in Human Monocyte Cell Line (THP-1)

(1) Experimental Method

THP-1 cells were seeded at a density of $2.0\times10^5$ cells/mL in 50 mL of RPMI1640 medium containing 10% FBS and 0.05 mM mercaptoethanol in a 75-$cm^2$ flask, and precultured for 48 hours.

The precultured THP-1 cells were harvested by centrifugation and suspended at $2.0\times10^6$ cells/mL in RPMI1640 medium containing 10% FBS and 0.05 mM mercaptoethanol, and the cell suspension was added to a 24-well plate at 500 μL/well. Test peptides were separately dissolved in the same medium as above, and 500 μL of each of the solutions was added to separate wells containing the cell suspension.

After overnight culture, the cells were harvested by centrifugation and washed twice with PBS containing 0.1% BSA (FACS buffer). The cells were then dispersed in 600 μL of FACS buffer containing 0.01% human γ-globulin solution (Sigma, G2388), and incubated at 4° C. for 10 minutes for blocking of Fc receptors.

After that, the cell suspension was divided into three 180-μL aliquots in 1.5-mL tubes, the tubes were centrifuged, and the cell pellets were prepared for the reaction with antibodies. To the cell pellets, FITC-labeled antibody solutions separately diluted to appropriate concentrations in FACS buffer were added in a volume of 50 μL, and incubation was performed at 4° C. for 30 minutes. The antibodies used were CD86 antibody (Pharmingen; Cat#555657), CD54 antibody (Dako; Cat# F7143) and isotype control (Mouse IgG) antibody (Dako; Cat# X0927). After the 30-minute incubation, the cells were harvested by centrifugation and washed twice with FACS buffer. The cells harvested by centrifugation were dispersed in 200 μL of FACS buffer containing 0.625 μg/mL propidium iodide, and the expression levels of the cell surface antigens on $1\times10^4$ viable cells were measured by flow cytometry. Forward and side scatter gating was not used for the analysis, and the relative fluorescence intensity (RFI) was calculated from the measured mean fluorescence intensities (MFI) by the following formula.

$$RFI\ (\%) = \frac{MFI \text{ of test substance-treatment cells} - MFI \text{ of test substance-treatment cells stained with isotype control}}{MFI \text{ of vehicle-treatment cells} - MFI \text{ of vehicle-treatment cells stained with isotype control}} \times 100$$

$MFI$: Geometric Mean Fluorescence Intensity (2) Results

Figure 3:
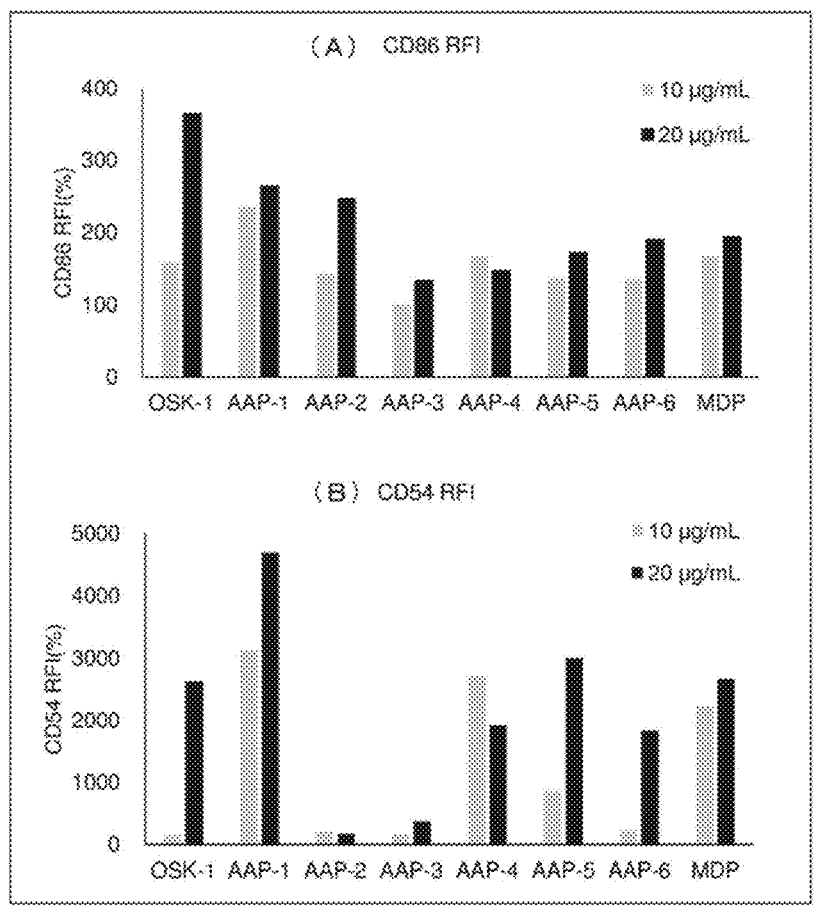
FIG. 3 shows the results of the measurement of the expression levels of CD86 and CD54 in the THP-1 cells cultured in the presence of OSK-1 or in the presence of any of AAP-1 to AAP-6. Panel A shows the results of CD86 and panel B shows the results of CD54.

The expression levels of CD86 and CD54 in the THP-1 cells cultured in the presence of OSK-1 or in the presence of any of AAP-1 to AAP-6 are shown in FIGS. 3A and 3B.

Figure 9:
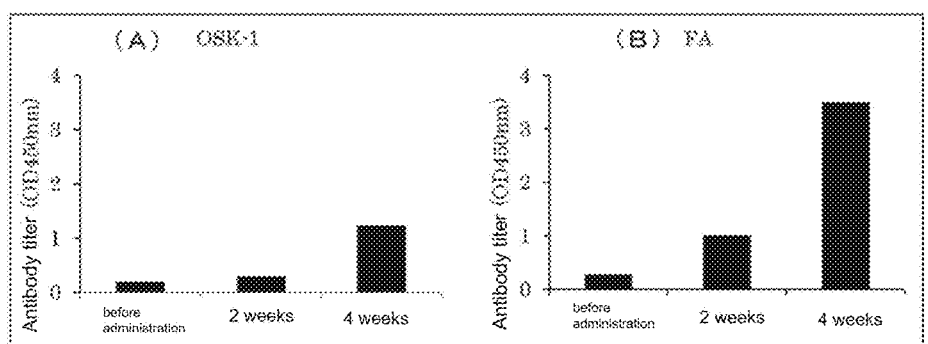
FIG. 9 shows the comparison of the adjuvant effects of OSK-1 and Freund's adjuvant (FA) in dogs. Panel A shows the results for the OSK-1 group and panel B shows the results for the FA group.
Figure 10:
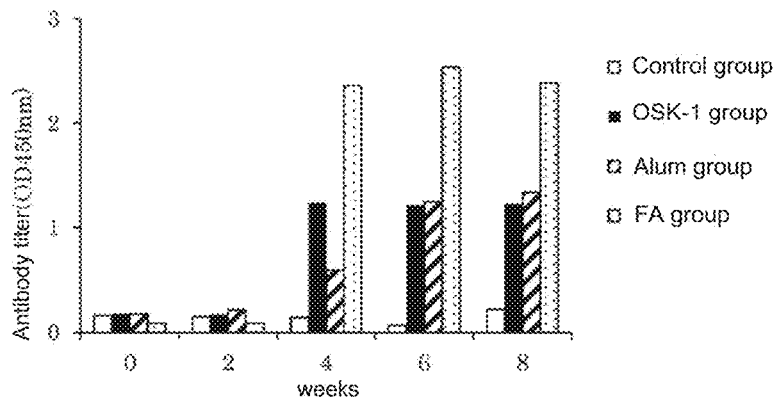
FIG. 10 shows the comparison of the adjuvant effects of OSK-1, alum and Freund's adjuvant (FA) in mice.

The addition of OSK-1 strongly induced the expression of CD86 and CD54 in the THP-1 cells. As shown by the results on the modified sequences of OSK-1 in which the C-terminal amino acids (LKRK or KRLKRK) of the sequence of OSK-1 were deleted (AAP-2 and AAP-3), the sequence with a smaller number of amino acids had a tendency to be considerably less active in inducing CD86 and CD54 expression. This tendency was particularly remarkable in inducing CD54 expression. For the modified sequence of OSK-1 in which the two C-terminal amino acids of OSK-1 were deleted (AAP-1) and the modified sequences of OSK-1 in which one, two or three amino acids from each of the N- and C-termini of OSK-1 were deleted (AAP-4 to AAP-6), no considerable reduction in the activity was observed as compared with the activity of OSK-1. The activity of OSK-1 to induce the expression of CD86 and CD54 was shown to be comparable or superior to that of muramyl dipeptide (MDP), a peptide with adjuvant activity (FIG. 9 and FIG. 10). The above results indicate that the C-terminal residue "L" of the amino acid sequence LHRLKRLRKRL (SEQ ID NO: 1) is essential for the immunostimulatory effect of the peptide of the present invention.

Figure 4:
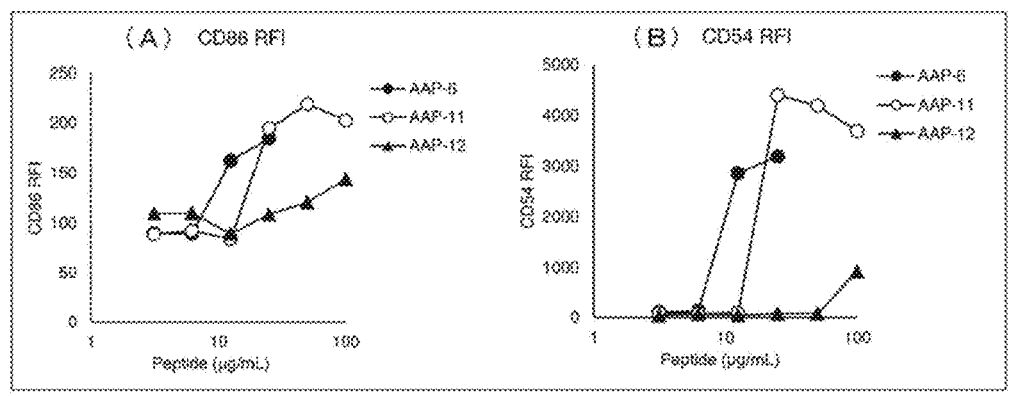
FIG. 4 shows the results of the measurement of the expression levels of CD86 and CD54 in the THP-1 cells cultured in the presence of AAP-6, AAP-11 or AAP-12. Panel A shows the results of CD86 and panel B shows the results of CD54.

The expression levels of CD86 and CD54 in the THP-1 cells cultured in the presence of AAP-6, AAP-11 or AAP-12 are shown in FIGS. 4A and 4B.

Figure 11:
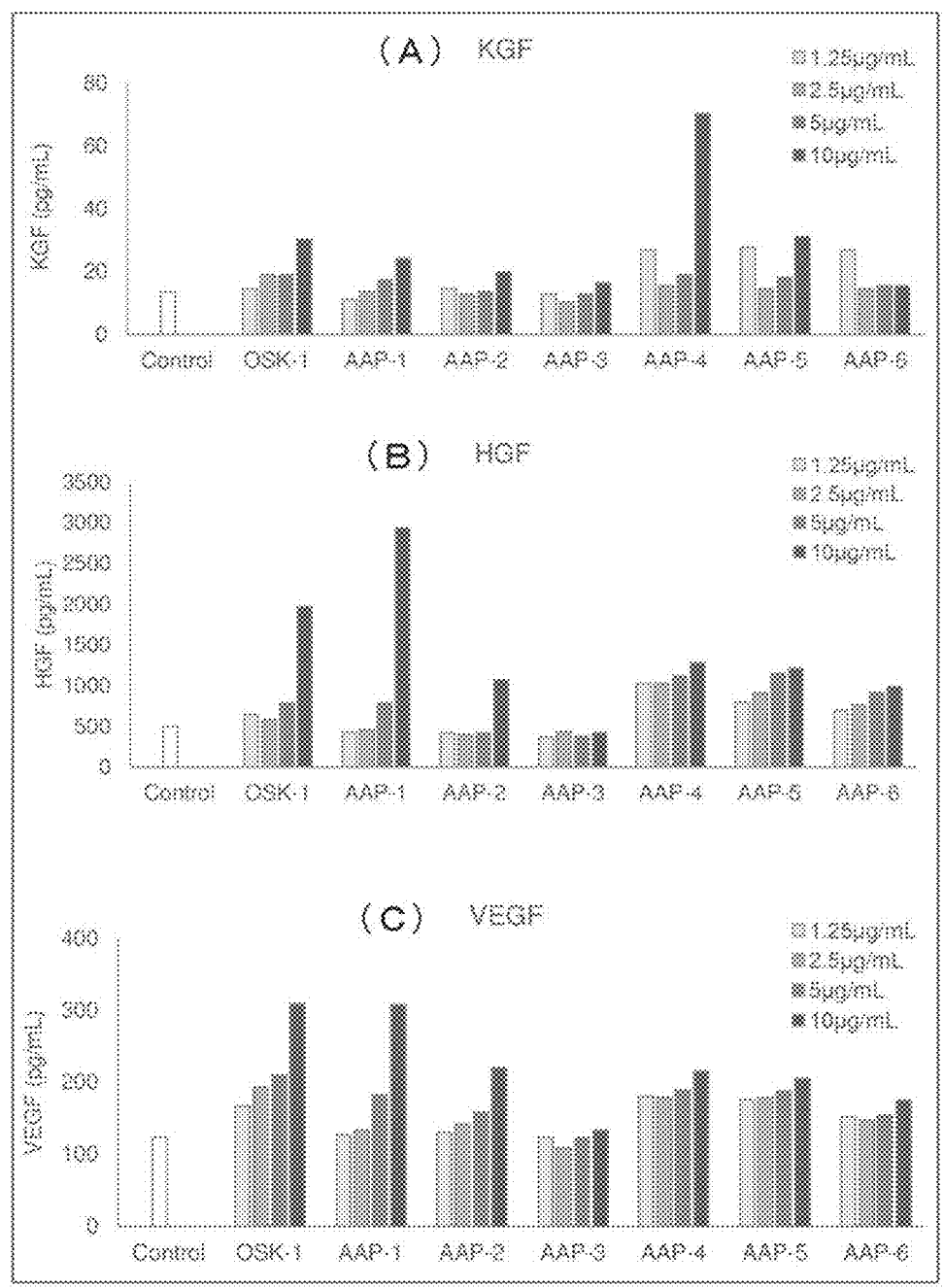
FIG. 11 shows the results of the measurement of the growth factor concentrations in the culture supernatant of the human hair follicle dermal papilla cells stimulated with OSK-1 or with any of AAP-1 to AAP-6. Panel A shows the results of KGF, panel B shows the results of HGF, and panel C shows the results of VEGF.
Figure 12:
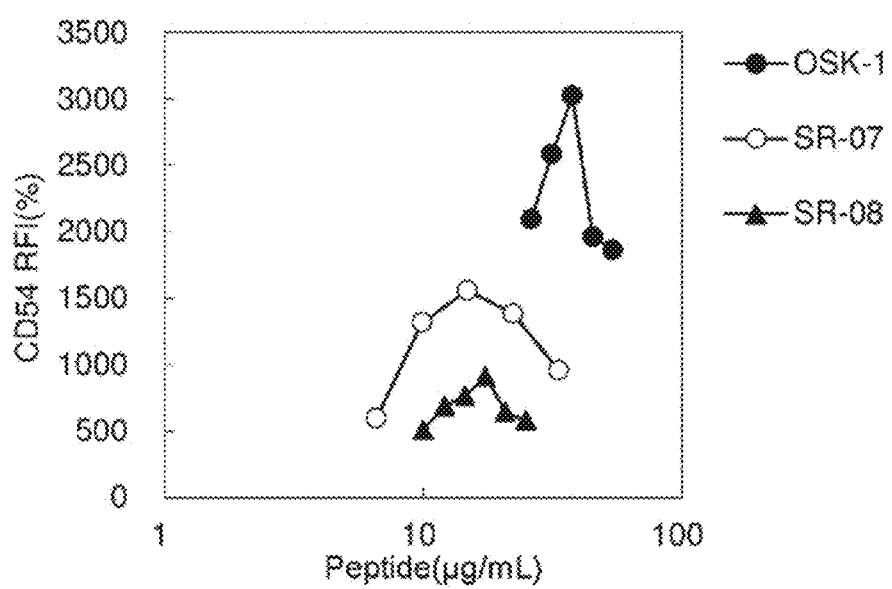
FIG. 12 shows the comparison of the effects of OSK-1 and its analogous peptides to induce CD54 expression in THP-1 cells.

The modified sequence of OSK-1 in which the seven N-terminal amino acids of the sequence of OSK-1 were deleted (AAP-12) had a tendency to be considerably less active than OSK-1 in inducing CD86 and CD54 expression. For the modified sequence of OSK-1 in which the three N-terminal amino acids and the three C-terminal amino acids of OSK-1 were deleted (AAP-6) and the modified sequence of OSK-1 in which the five N-terminal amino acids and the three C-terminal amino acids were deleted (AAP-11), no considerable reduction in the activity was observed as compared with the activity of OSK-1 (FIG. 11 and FIG. 12). The above results indicate that the N-terminal residue "L" of the amino acid sequence LHRLKRLRKRL (SEQ ID NO: 1) is essential for the immunostimulatory effect of the peptide of the present invention.

Example 5: Effect of OSK-1 to Activate Inflammasomes (1)

(1) Experimental Method

THP-1 cells were transfected with a siRNA against the inflammasome component NLRP3 (NOD-like receptor family, pyrin domain containing 3) (final concentration: 100 nM, Hs_CIAS 1_6 and Hs_CIAS 1_9, manufactured by QIAGEN) or a control siRNA using a transfection reagent (6 μL/well, HiPerFect Transfection Reagent, manufactured by QIAGEN). After overnight culture, the expression level of NLRP3 was determined by western blotting.

Each type of the THP-1 cells was suspended at $1 \times 10^6$ cells/mL in RPMI1640 medium containing 1 μg/mL LPS and 10% FBS, and incubated in a $CO_2$ incubator for 3 hours for cell priming. The cell suspension was centrifuged, the cells were resuspended at $1 \times 10^6$ cells/mL in RPMI1640 medium containing 10% FBS, and the cell suspension was added to a 24-well plate at 500 μL/well. An OSK-1 solution was prepared at a 2-fold higher concentration than the final concentration in RPMI1640 medium containing 10% FBS and added to the plate at 500 μL/well. After 16 hours, the culture supernatant was harvested, and the IL-1β and TNFα concentrations in the supernatant were measured by ELISA.

(2) Results

Figure 5:
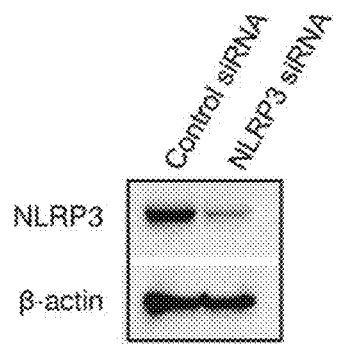
FIG. 5 shows the expression level of NLRP3 determined by western blotting.

The expression level of NLRP3 determined by western blotting is shown in FIG. 5. The expression of NLRP3 was knocked down in the THP-1 cells transfected with the siRNA against NLRP3.

Figure 6:
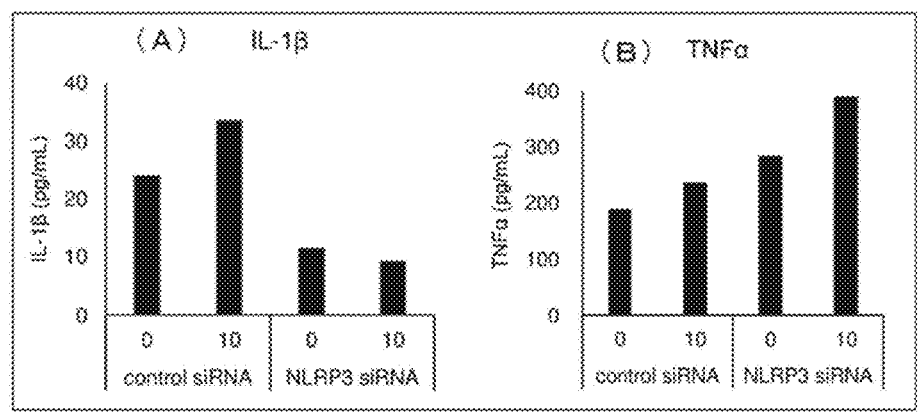
FIG. 6 shows the comparison of the production levels of IL-1β and TNFα in the THP-1 cells which had been transfected with a siRNA against NLRP3 or a control siRNA and cultured in the presence of OSK-1 at a concentration of 10 μg/mL. Panel A shows the results of IL-1β and panel B shows the results of TNFα.

The comparison of the production levels of IL-1β and TNFα in the NLRP3-knockdown THP-1 cells and the control THP-1 cells cultured in the presence of OSK-1 at a concentration of 10 μg/mL is shown in FIGS. 6A and 6B. The production of IL-1β was induced by OSK-1 in the cells not subjected to knockdown of NLRP3 expression (the cells transfected with the control siRNA), but in the NLRP3-knockdown cells, the induction of IL-1β production by OSK-1 was inhibited. On the other hand, the production of TNFα, which does not participate in the inflammasome activation, was induced by OSK-1 regardless of whether NLRP3 expression was knocked down or not.

Example 6: Effect of OSK-1 to Activate Inflammasomes (2)

(1) Experimental Method

THP-1 cells were suspended at $1 \times 10^6$ cells/mL in RPMI1640 medium containing 1 μg/mL LPS and 10% FBS, and incubated in a $CO_2$ incubator for 3 hours for cell priming. The cell suspension was centrifuged, the cells were resuspended at $1 \times 10^6$ cells/mL in RPMI1640 medium containing 10% FBS, and the cell suspension was added to a 96-well plate at 100 μL/well. The cathepsin B inhibitor Ca-074-Me (final concentration: 10 μM), the caspase-1 inhibitor Z-YVAD-FMK (final concentration: 10 μM) or the medium was added to the wells. After that, OSK-1 or the medium was added to the wells, and the cells were cultured in a $CO_2$ incubator. After 16 hours, the culture supernatant was harvested, and the cytokine concentrations in the supernatant were measured by ELISA.

(2) Results

Figure 7:
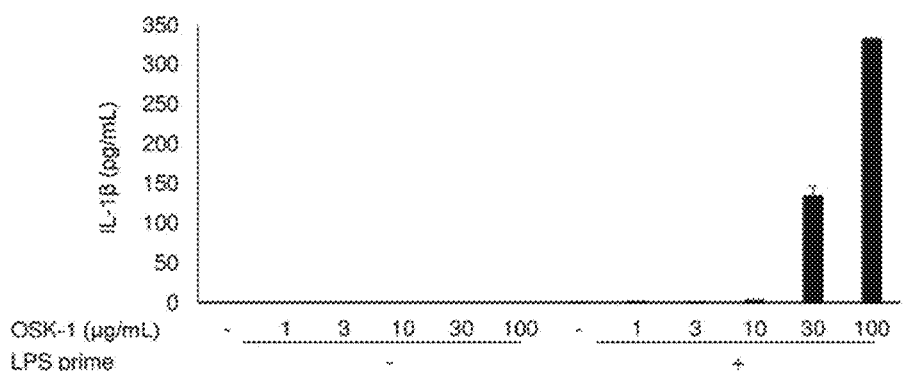
FIG. 7 shows the comparison of the effect of OSK-1 on IL-1β production in LPS-primed THP-1 cells and non-primed THP-1 cells.

The comparison of the effect of OSK-1 on IL-1β production in the LPS-primed THP-1 cells and the non-primed THP-1 cells is shown in FIG. 7. OSK-1 induced the production of IL-1β only in the LPS-primed THP-1 cells.

Figure 8:
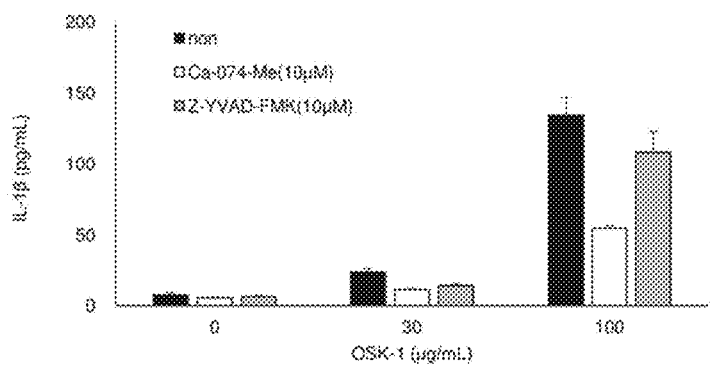
FIG. 8 shows the comparison of the effect of OSK-1 on IL-1β production in the presence of a cathepsin B inhibitor or a caspase-1 inhibitor and in the absence of both of them.

The comparison of the effect of OSK-1 on IL-1β production in the presence of the cathepsin B inhibitor or the caspase-1 inhibitor and in the absence of both of them is shown in FIG. 8. The induction of IL-1β production by OSK-1 was inhibited by Ca-074-Me, which is an inhibitor of the inflammasome activator cathepsin B, and also inhibited by Z-YVAD-FMK, which is an inhibitor of the inflammasome component caspase-1.

The above results indicate that proIL-1β expressed in the LPS-primed cells was exposed to the inflammasome component caspase-1 activated by OSK-1 and thereby processed into IL-1β, which was then released from the cells.

Example 7: Confirmation of Adjuvant Effect (Effect of Enhancing the Immunogenicity of Vaccine Antigen) of OSK-1 in Dogs (1) Experimental Method The adjuvant effect of OSK-1 was compared with that of the conventional Freund's adjuvant in dogs. Ang II-KLH (angiotensin II-keyhole limpet hemocyanin) as a vaccine (25 μg/animal) and OSK-1 (500 μg/animal) or Freund's adjuvant (250 μL/animal) as an adjuvant were intracutaneously administered to beagles twice at a 2-week interval (2 animals per group). For the Freund's adjuvant group, complete Freund's adjuvant was used at the first administration, and incomplete Freund's adjuvant was used at the second administration. Blood was drawn before the first administration and 2 and 4 weeks after the first administration, and the anti-Ang II antibody titer was measured.

The serum separated from the blood was serially diluted in 5% skim milk/PBS, and the diluted sera were added to an Ang II-BSA-coated 96-well ELISA plate. The plate was allowed to stand at 4° C. overnight. The wells were washed with PBS-T, and an HRP-labeled anti-mouse IgG antibody diluted in 5% skim milk/PBS was added to the wells. The plate was incubated with agitation at room temperature for 3 hours. The wells were washed with PBS-T, and a TMB solution was added to the wells. The plate was allowed to stand under protection from light for 30 minutes, and 0.5 N $H_2SO_4$ was added to the wells to stop the reaction. The absorbance at 450 nm was measured and used for antibody titer comparison.

(2) Results

The results are shown in FIG. 9. Panel A shows the results for the OSK-1 group and panel B shows the results for the Freund's adjuvant (FA) group. The increase in the anti-Ang II antibody titer was observed in the animals of the OSK-1 group.

Example 8: Confirmation of Adjuvant Effect (Effect of Enhancing the Immunogenicity of Vaccine Antigen) of OSK-1 in Mice (1) Experimental Method The adjuvant effect of OSK-1 was compared with that of alum or Freund's adjuvant in mice. Ang II-KLH as a vaccine (2 μg/animal) and OSK-1 (100 μg/animal), alum (400 μg/animal) or Freund's adjuvant (50 μg/animal) as an adjuvant were intracutaneously administered to C57/BL6 mice 3 times at 2-week intervals (3 animals per group). For the Freund's adjuvant group, complete Freund's adjuvant was used at the first administration, and incomplete Freund's adjuvant was used at the second and third administration. Blood was drawn before the first administration and 2, 4, 6 and 8 weeks after the first administration, and the anti-Ang II antibody titer was measured.

The antibody titer was measured in the same manner as in Example 7.

(2) Results

The comparison of the adjuvant effects of OSK-1, alum and Freund's adjuvant (FA) is shown in FIG. 10. The increase in the anti-Ang II antibody titer was observed in the OSK-1 group. This increase was smaller than that in the Freund's adjuvant (FA) group, but comparable to that in the alum group.

Example 9: Effect of Promoting the Production of Growth Factors for Hair Follicle Dermal Papilla Cells (1)

(1) Experimental Method

Human hair follicle dermal papilla cells in DMEM medium containing 10% FBS were seeded at 3×10⁴ cells/well on a 24-well plate and cultured in a $CO_2$ incubator overnight. On the following day, the medium was removed, test peptide solutions in DMEM medium containing 1% FBS were added to the plate, and the cells were cultured in a $CO_2$ incubator for 5 days. The culture supernatant was harvested, and the KGF, HGF and VEGF concentrations in the culture supernatant were measured by ELISA.

(2) Results

The results of the ELISA measurement of the KGF, HGF and VEGF concentrations in the culture supernatant of the human hair follicle dermal papilla cells stimulated with various test peptides are shown in FIGS. 11A to 11C. OSK-1 promoted the production of the indicated growth factors in a concentration dependent manner. AAP-1 and AAP-4 to AAP-6 also promoted the production of the indicated growth factors in a concentration dependent manner as with OSK-1. The modified sequences of OSK-1 in which the C-terminal amino acids (LKRK or KRLKRK) of the sequence of OSK-1 were deleted (AAP-2 and AAP-3) were less effective than OSK-1 for promoting the production of the indicated growth factors, in particular, HGF. The above results indicate that the C-terminal residue "L" of the amino acid sequence LHRLKRLRKRL (SEQ ID NO: 1) is essential for the effect of the peptide of the present invention to promote the production of the growth factors.

Example 10: Comparison of Effect of Inducing CD54 Expression Between OSK-1 and its Analogous Peptides (SR-07 and SR-08)

OSK-1 and its analogous peptides (SR-07 and SR-08) were compared in terms of the effect of inducing CD54 expression. The experimental method was the same as that in Example 4. SR-07 and SR-08 are peptides described in WO 2010/137594 and their sequences are shown in Table 2 below.

TABLE 2

| Peptide | N-terminus | 1 | 2 | 3 | 4 | 5 | 6 | 7 | 8 | 9 | 10 | 11 | 12 | 13 | 14 | 15 | 16 | 17 | 18 | 19 | 20 | SEQ ID NO: | C-terminus |
|---|---|---|---|---|---|---|---|---|---|---|---|---|---|---|---|---|---|---|---|---|---|---|---|
| OSK-1 | Acetyl | E | L | K | L | I | F | L | H | R | L | K | R | L | R | K | R | L | K | R | K | SEQ ID NO: 2 | amide |
| SR-07 | | M | L | K | L | I | F | L | H | R | L | K | R | M | R | K | R | L | dK | R | K | SEQ ID NO: 12 | |
| SR-08 | | | L | K | L | I | F | L | H | R | L | K | R | M | R | K | R | L | dK | R | K | SEQ ID NO: 13 | amide |

* dK: D-isomer

When the viability of the non-treated control cells (vehicle treatment cells) was 90% or more, the test was considered valid. In the case where the cell viability at a particular sample concentration used in the test was lower than 50%, the data of the CD54 level at the concentration was excluded from the evaluation.

The results are shown in FIG. 12. OSK-1 was more highly active for inducing CD54 expression than SR-07 and SR-08.

Example 11: Effect on Cytokine Production in Human Monocyte Cell Line (THP-1) (3)

(1) Experimental Method

The experiment in this example was performed in the same manner as in Example 3, and the IL-1β, IL-18, TNFα, IL-6, RANTES, MIP-1α and MIP-1β concentrations in the culture supernatant were measured.

(2) Results

The results are shown in FIGS. 15A to 15G. The addition of OSK-1 induced the production of the chemokines and cytokines in the PMA-differentiated THP-1 cells in an OSK-1 concentration dependent manner.

Example 12: Effect on Cytokine Production in Mouse Macrophage Cells (RAW 264.7)

(1) Experimental Method

RAW 264.7 cells were suspended at 1×10⁶ cells/mL in DMEM medium containing 50 ng/mL LPS and 10% FBS, and incubated in a $CO_2$ incubator for 3 hours for cell priming. The cell suspension was centrifugated, the cells were resuspended at 1×10⁶ cells/mL in DMEM medium containing 10% FBS, and the cell suspension was added to a 24-well plate at 500 μL/well. An OSK-1 solution was prepared at a 2-fold higher concentration than the final concentration in DMEM medium containing 10% FBS and added to the plate at 500 μL/well. After about 16 hours, the culture supernatant was harvested, and the cytokine concentrations in the supernatant were measured by ELISA.

(2) Results

The results of the measurement of the IL-1β, IL-18, TNFα and IL-6 concentrations in the culture supernatant are shown in FIGS. 16A to 16D.

The addition of OSK-1 induced the production of the cytokines in the LPS-primed RAW 264.7 cells in an OSK-1 concentration dependent manner.

Example 13: Effect on Cytokine Production in Mouse Bone Marrow-Derived Dendritic Cells (1) Experimental Method Bone marrow cells were harvested from the thigh bone of a C57BL/6 mouse, seeded in RPMI1640 medium containing 20 mg/mL GM-CSF (granulocyte macrophage colony-stimulating factor) and 10% FBS, and cultured for 3 days. After the 3-day culture, a fresh medium was added and culture was continued for additional 4 days. The cells not adherent on the culture plate were harvested and regarded as bone marrow-derived dendritic cells. The cells were suspended at $2\times10^6$ cells/mL in RPMI1640 medium containing 10% FBS, and the cell suspension was added to a 24-well plate at 500 μL/well. An OSK-1 solution was prepared at a 2-fold higher concentration than the final concentration in RPMI1640 medium containing 10% FBS and added to the plate at 500 μL/well. After about 16 hours, the culture supernatant was harvested, and the cytokine concentrations in the supernatant were measured by ELISA.

(2) Results

The results of the measurement of the IL-1β, IFNγ, TNFα, IL-6 and IL-12p70 concentrations in the culture supernatant are shown in FIGS. 17A to 17E.

The addition of OSK-1 induced the production of the cytokines in the mouse bone marrow-derived dendritic cells in an OSK-1 concentration dependent manner.

Example 14: Effect on Cytokine Production in Human Monocyte Cell Line (THP-1) (Comparison with Alum and CpG Nucleotide)

(1) Experimental Method

THP-1 cells were suspended at $1\times10^6$ cells/mL in RPMI1640 medium containing 1 μg/mL LPS and 10% FBS, and incubated in a $CO_2$ incubator for 3 hours for cell priming. The cell suspension was centrifuged, the cells were resuspended at $1\times10^6$ cells/mL in RPMI1640 medium containing 10% FBS, and the cell suspension was added to a 24-well plate at 500 μL/well. An OSK-1 solution, an alum (Alhydrogel 2%, InvivoGen) solution and a CpG nucleotide (CpG ODN 2006, Novus Biologicals) solution were prepared at 2-fold higher concentrations than the final concentrations in RPMI1640 medium containing 10% FBS and added to the plate at 500 μL/well. After about 16 hours, the culture supernatant was harvested, and the cytokine concentrations in the supernatant were measured by ELISA.

(2) Results

The results of the measurement of the IL-1β, IL-18, TNFα and IL-6 concentrations in the culture supernatant are shown in FIGS. 18A to 18D.

The addition of OSK-1 more strongly induced the production of IL-1β, IL-18 and TNFα in the LPS-primed THP-1 cells as compared with the addition of alum or the CpG nucleotide. As for the production of IL-18, although OSK-1 was less effective than alum, OSK-1 significantly induced the production of IL-18.

Example 15: Effect on CD86 and CD54 Expression in Human Monocyte Cell Line (THP-1) (Comparison with Alum)

(1) Experimental Method

The experiment in this example was performed in the same manner as in Example 4 except for using OSK-1 as the test peptide and alum as the control.

(2) Results

Figure 19:
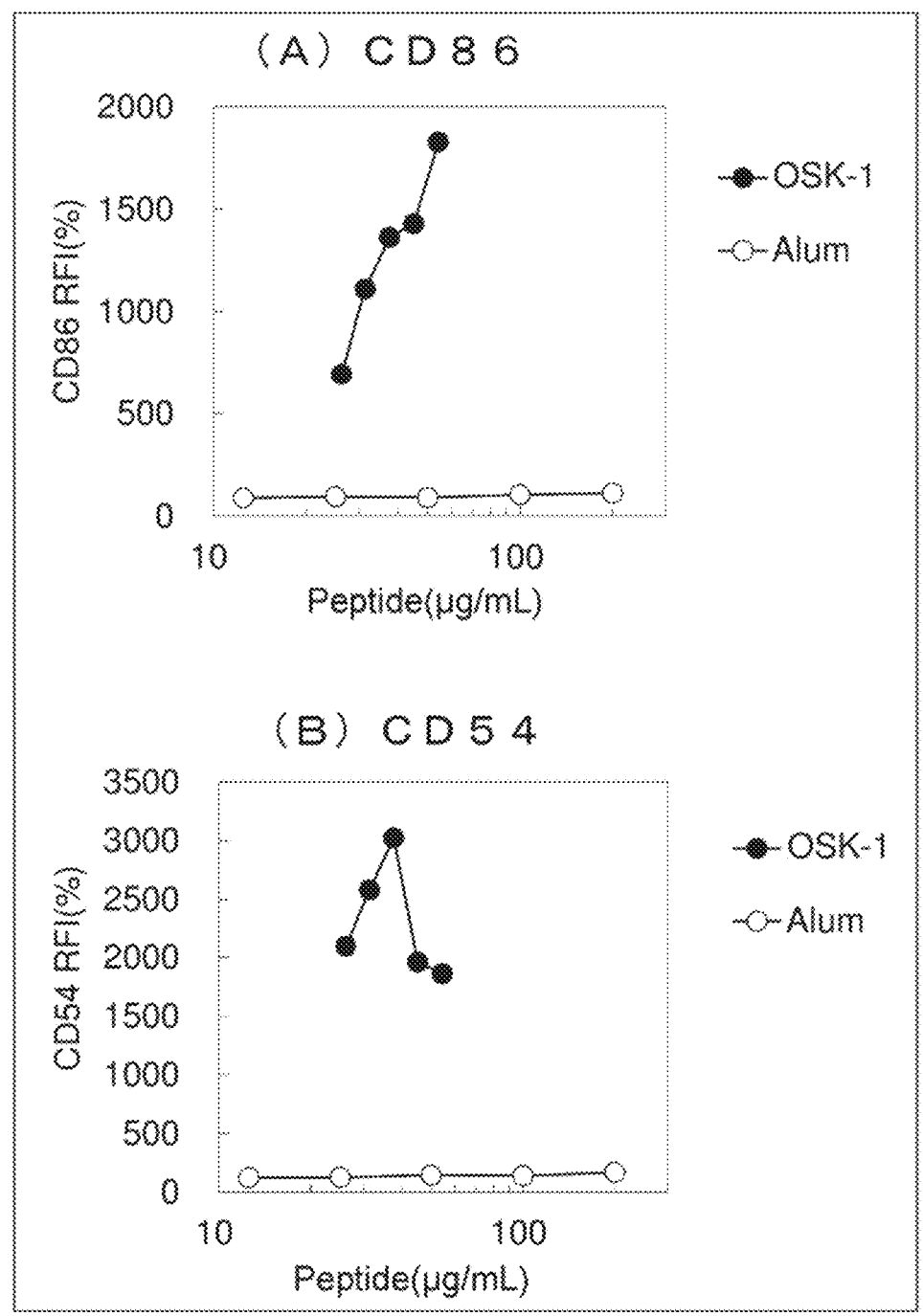
FIG. 19 shows the results of the measurement of the expression levels of CD86 and CD54 in the THP-1 cells cultured in the presence of OSK-1 or alum. Panel A shows the results of CD86 and panel B shows the results of CD54.

The expression levels of CD86 and CD54 in the THP-1 cells cultured in the presence of OSK-1 or alum are shown in FIGS. 19A and 19B.

The addition of OSK-1 strongly induced CD86 and CD54 expression in the THP-1 cells. On the other hand, the addition of alum did not induce CD86 or CD54 expression in the THP-1 cells.

Example 16: Activation of NFκB by OSK-1 in Human Monocyte Cell Line (THP-1)

(1) Experimental Method

THP-1 cells were diluted to $5\times10^5$ cells in 500 μL of RPMI1640 medium containing 10% FBS, and the cell suspension was added to a 24-well plate at 500 μL/well. QNZ (Enzo, final concentration: 10 μM) in RPMI1640 medium containing 10% FBS, BAY11-7082 (Enzo, final concentration: 10 μM) in RPMI1640 medium containing 10% FBS and RPMI1640 medium containing 10% FBS were added to the plate, and the cells were cultured for 2.5 hours. OSK-1 was added to the wells at a final concentration of 100 ng/mL, and the cells were cultured for 2 hours. After that, the culture supernatant was harvested, and the TNFα concentration in the supernatant was measured by ELISA.

(2) Results

Figure 20:
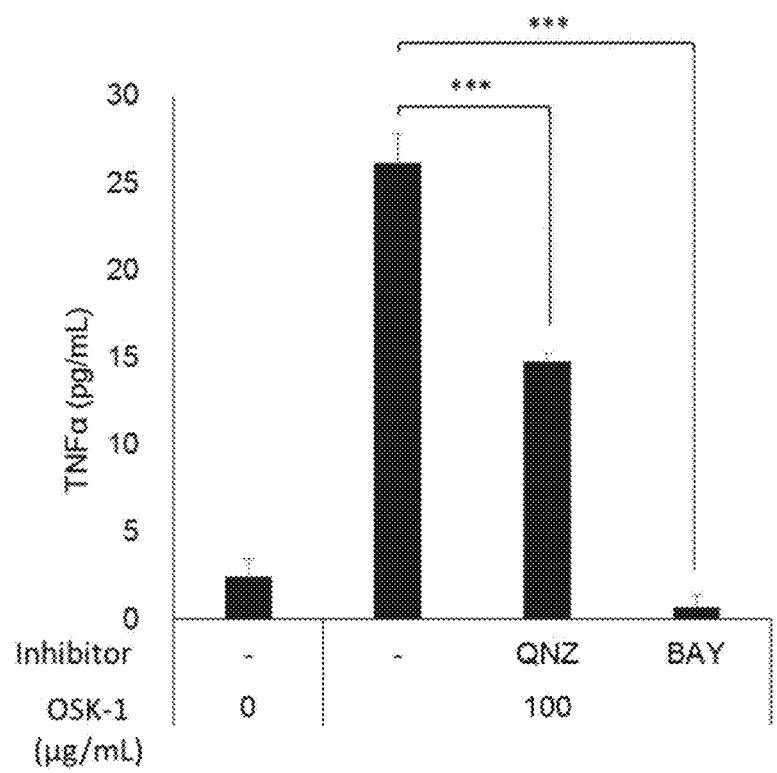
FIG. 20 shows the effect of OSK-1 to activate NFκB in THP-1 cells.

The results are shown in FIG. 20. OSK-1 induced the production of TNFα in the THP-1 cells, but the production of TNFα induced by OSK-1 was inhibited in the presence of the NFκB inhibitor QNZ or BAY11-7082. These results show that OSK-1 is effective for activating NFκB.

Example 17: Antibody Production Induced by OSK-1-Angiotensin II Conjugate Vaccine (1) Experimental Method The OSK-1 peptide and an angiotensin II peptide were conjugated via ε-Acp as a spacer to form an "OSK-1-Ang II conjugate vaccine". The OSK-1-Ang II conjugate vaccine was evaluated for the induction of antibody production in mice. Mice were divided into the following 3 groups: (1) Ang II-KLH (5 μg/mouse)+alum (Alhydrogel 2%, InvivoGen, 0.4 mg/mouse), (2) OSK-1-Ang II conjugate vaccine (10 μg/mouse), and (3) OSK-1-Ang II conjugate vaccine (50 μg/mouse). In each group, the test substance was intracutaneously administered to Balb/c mice 3 times at 2-week intervals (6 animals per group). Blood was drawn before the first administration and 2, 4, 6 and 8 weeks after the first administration, and the anti-Ang II antibody titer was measured by ELISA. The IgG subtype of the produced antibody was analyzed by ELISA.

(2) Results

Figure 21:
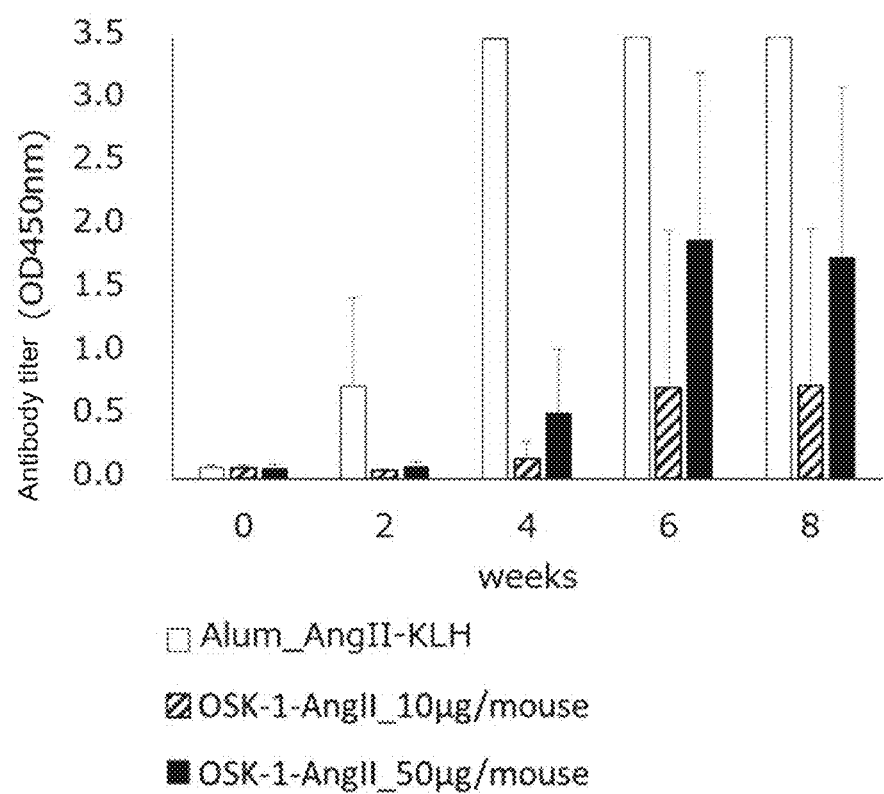
FIG. 21 shows the results of the evaluation of the effect of administration of an OSK-1-angiotensin II conjugate vaccine on antibody production in mice.
Figure 22:
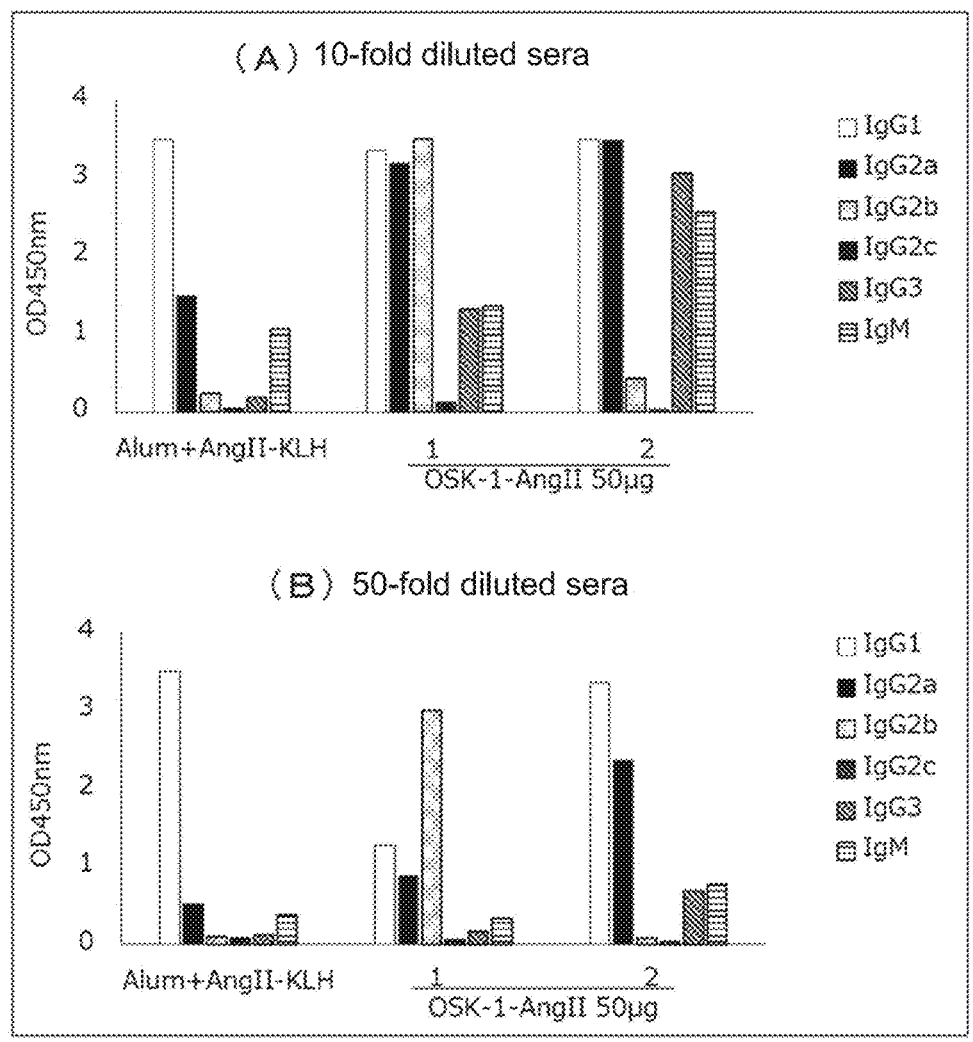
FIG. 22 shows the results of the subtype analysis of the antibody produced by the mice subjected to the administration of an OSK-1-angiotensin II conjugate vaccine. Panel A shows the results of the analysis using 10-fold diluted sera and panel B shows the results of the analysis using 50-fold diluted sera.

The results of the measurement of the anti-Ang II antibody titer are shown in FIG. 21, and the results of the analysis of the IgG subtype of the produced antibody are shown in FIGS. 22A and 22B.

The OSK-1-Ang II conjugate vaccine induced anti-Ang II antibody production in a concentration dependent manner.

As shown by the results of the IgG subtype analysis, the mice subjected to the co-administration of the Ang II-KLH vaccine and the Th2-type adjuvant alum dominantly produced IgG1, which is a Th2-type antibody, while the mice subjected to the administration of the OSK-1-Ang II conjugate vaccine produced not only a large amount of IgG1, which is a Th2-type IgG, but also large amounts of IgG2a, IgG2b and IgG3, all of which are Th1-type IgGs.

Example 18: Induction of WT1-Specific Immunity by OSK-1-WT1 Conjugate Vaccine (1) Experimental Method The OSK-1 peptide and a WT1 peptide were conjugated via ε-Acp as a spacer to form an "OSK-1-WT1 conjugate vaccine". The OSK-1-WT1 conjugate vaccine was evaluated for the ability to induce WT1-specific immunity in mice. Mice were divided into the following 5 groups (3 animals per group): (1) physiological saline, (2) WT1 peptide (15 μg/mouse)+Incomplete Freund's Adjuvant (IFA, SIGMA; Cat#F5506, 50 μL/mouse), (3) WT1 peptide (15 μg/mouse)+OSK-1 (100 μg/mouse), (4) OSK-1-WT1 conjugate vaccine (50 μg/mouse), and (5) OSK-1-WT1 conjugate vaccine (300 μg/mouse). In each group, the test substance was administered to C57BL/6 mice once a week for 4 weeks. At 2 weeks after the 4th administration, the spleen was excised from each immunized mouse, and the ELISpot assay was performed. The specific procedure is as follows. Splenocytes were prepared from the excised spleen and seeded on a filter plate coated with an anti-IL-4 antibody or an anti-IFNγ antibody. The WT1 peptide or the OSK-1-WT1 peptide was added to the wells, and the splenocytes were cultured for 3 days. After that, each well of the filter plate was stained and the spots of IL-4- or IFNγ-producing cells was counted.

(2) Results

In group (3), in which WT1 plus OSK-1 as an adjuvant had been administered to mice, and groups (4) and (5), in which the conjugate of OSK-1 and WT1 had been administered to mice, more cells produced IFNγ in response to the stimulation with the WT1 peptide. In particular, group (5) showed a greater response to the stimulation. On the other hand, in group (2), in which WT1 plus IFA as an adjuvant had been administered to mice, more cells produced IL-4 in response to the stimulation with the WT1 peptide.

Example 19: Effect of Promoting the Production of Growth Factors for Hair Follicle Dermal Papilla Cells (2)

(1) Experimental Method

In this experiment, OSK-1 and AAP-11 were used as the test peptides, and the concentrations of KGF, HGF and VEGF were measured in the same manner as in Example 9.

(2)

Figure 23:
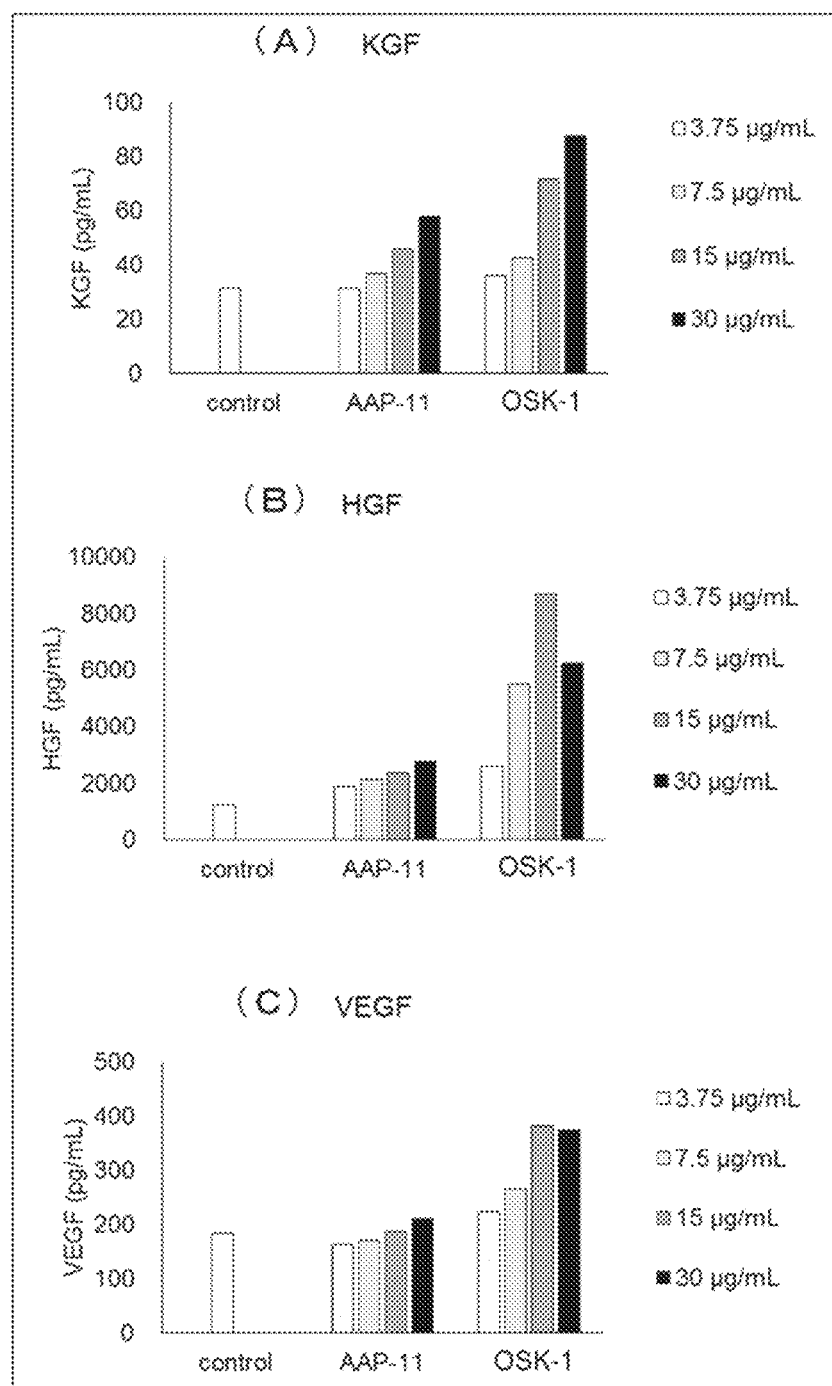
FIG. 23 shows the results of the measurement of the growth factor concentrations in the culture supernatant of the human hair follicle dermal papilla cells stimulated with OSK-1 or AAP-11. Panel A shows the results of KGF, panel B shows the results of HGF, and panel C shows the results of VEGF.

The results are shown in FIG. 23. AAP-11 promoted the production of the indicated growth factors in a concentration dependent manner.

Example 20: Hair-Growth Effect of OSK-1

(1) Experimental Method

The dorsal skin of 8-week-old male C3H/HeN mice in the resting phase of the hair cycle was shaved using a hair clipper and a shaver with caution to avoid damage to the skin. The shaved area was 2×4 cm. To the shaved area, 100 μL of a 0.02% (w/v), 0.1% (w/v) or 0.5% (w/v) OSK-1 solution was applied once daily for 14 days starting from 3 days after the shaving. For the control group, physiological saline was applied, and for the positive control group, 3% (w/v) minoxidil was applied. The day of shaving was designated as Day 0. On Day 3, Day 7, Day 10, Day 14 and Day 17, the percentage of the area of hair regrowth relative to the entire shaved area in each mouse was scored according to the following criteria: 0% was defined as score 0, 20% or less was defined as score 1, 40% or less was defined as score 2, 60% or less was defined as score 3, 80% or less was defined as score 4, and 100% or less was defined as score 5. In addition, 10 strands of newly grown hair in the shaved area of each mouse were pulled out on Day 17, the length of each strand of newly grown hair was measured under a stereomicroscope, and the measured lengths were summed as the hair length (mm) of each animal.

(2) Results

Figure 24:
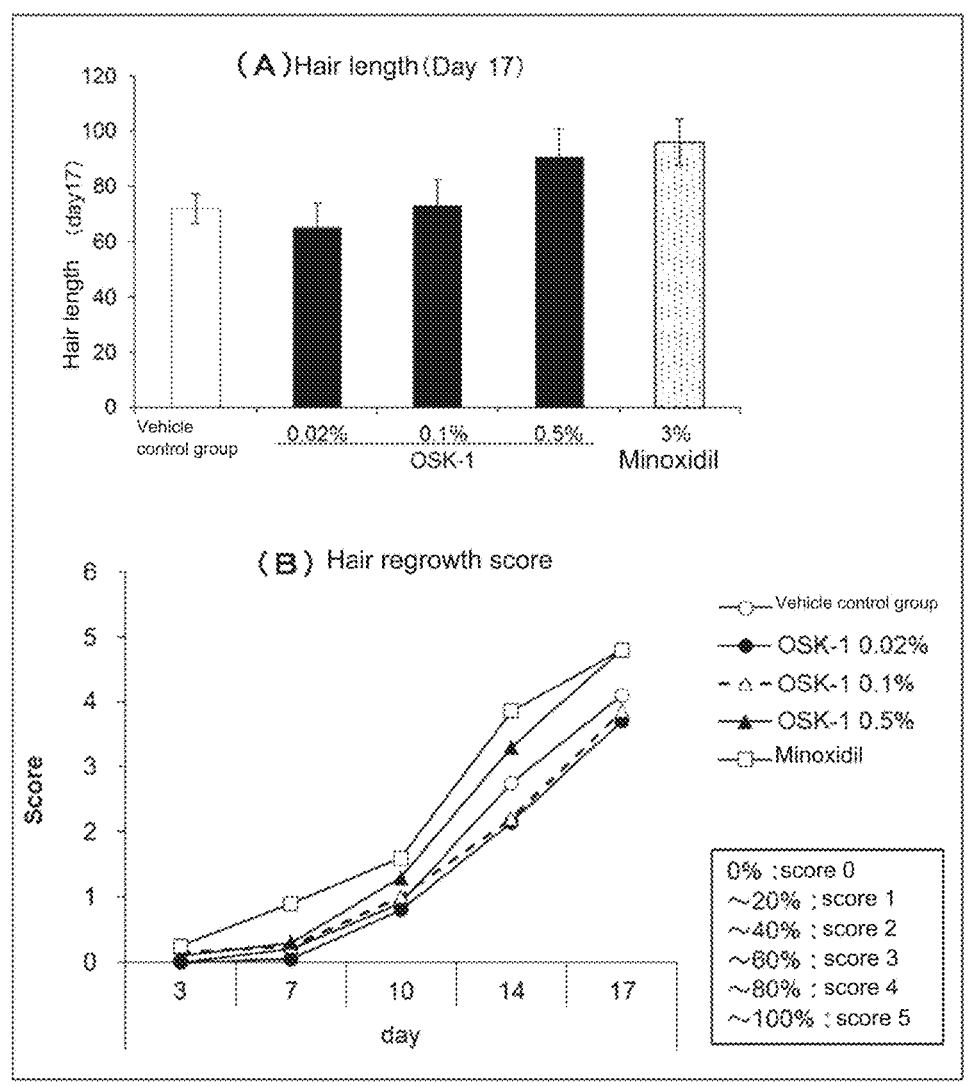
FIG. 24 shows the hair growth effect of OSK-1 in mice. Panel A shows the hair length on Day 17 and panel B shows the hair regrowth score.

The results are shown in FIG. 24. Panel A shows the hair length on Day 17 and panel B shows the score of the area of hair regrowth. OSK-1 was shown to promote hair growth in a concentration dependent manner. The hair regrowth score and the hair length in the 0.5% OSK-1 group were almost comparable to those in the 3% minoxidil group.

The present invention is not limited to the particular embodiments and examples described above, and various modifications can be made within the scope of the appended claims. Other embodiments provided by suitably combining technical means disclosed in separate embodiments of the present invention are also within the technical scope of the present invention. All the academic publications and patent literature cited in the description are incorporated herein by reference.

INDUSTRIAL APPLICABILITY

The peptide of the present invention has immunostimulatory effect and therefore can be used as an immunostimulant. Preferably, the peptide can be used as a vaccine adjuvant. A vaccine composition containing the peptide of the present invention enables more effective therapy. Moreover, the peptide of the present invention can preferably be used as an ingredient of cosmetics, quasi drugs, medicinal drugs, foods and drinks and dietary supplements intended to promote hair growth or regrowth.

---

The invention claimed is:

1. A method for hair growth or regrowth promotion, comprising administering an effective amount of a peptide of 23 or less amino acids comprising the amino acid sequence LHRLKRLRKRLK (SEQ ID NO: 9) to a mammal.

2. The method of claim 1, wherein the peptide comprises the amino acid sequence ELKLIFLHRLKRLRKRLKRK (SEQ ID NO: 2) or an amino acid sequence having 90% or more identity with the amino acid sequence ELKLIFLHRLKRLRKRLKRK.

3. The method of claim 2, wherein the peptide is amidated at the C-terminus.

4. The method of claim 3, wherein the peptide is acetylated at the N-terminus.

5. The method of claim 2, wherein the peptide is acetylated at the N-terminus.

6. The method of claim 1, wherein the peptide is amidated at the C-terminus.

7. The method of claim 6, wherein the peptide is acetylated at the N-terminus.

8. The method of claim 1, wherein the peptide is acetylated at the N-terminus.

* * * * *